(12) United States Patent
Daifuku et al.

(10) Patent No.: US 7,595,139 B2
(45) Date of Patent: Sep. 29, 2009

(54) METAL COMPLEX DYE, COLOR TONER AND COLOR FILTER

(75) Inventors: Koji Daifuku, Hachioji (JP); Takatugu Suzuki, Hachioji (JP); Kaori Ono, Hino (JP)

(73) Assignee: Konica Minolta Holdings, Inc., Tokyo (JP)

( * ) Notice: Subject to any disclaimer, the term of this patent is extended or adjusted under 35 U.S.C. 154(b) by 512 days.

(21) Appl. No.: 11/206,490

(22) Filed: Aug. 18, 2005

(65) Prior Publication Data

US 2006/0046177 A1    Mar. 2, 2006

(30) Foreign Application Priority Data

Aug. 26, 2004    (JP)    ............................. 2004-246428

(51) Int. Cl.
*G03G 9/09*    (2006.01)

(52) U.S. Cl. ................................. 430/108.21; 528/101

(58) Field of Classification Search ............ 430/108.21; 528/101
See application file for complete search history.

(56) References Cited

U.S. PATENT DOCUMENTS 4,757,046 A * 7/1988 Byers et al. ................. 503/227
6,255,029 B1 * 7/2001 Hirose et al. ........... 430/137.14
2005/0250645 A1 * 11/2005 Ono et al. ................... 503/227

FOREIGN PATENT DOCUMENTS

GB    1181951    *    2/1970

* cited by examiner

*Primary Examiner*—Mark F Huff
*Assistant Examiner*—Rachel L Burney
(74) *Attorney, Agent, or Firm*—Frishauf, Holtz, Goodman & Chick, P.C.

(57) ABSTRACT

A metal complex dye is disclosed, containing a dye as a ligand represented by the following formula (1). A color toner and a color filter containing the metal complex dye are also disclosed.

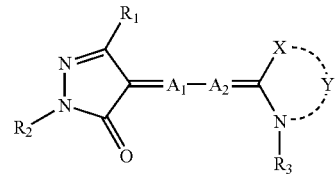

5 Claims, 6 Drawing Sheets

METAL COMPLEX DYE, COLOR TONER AND COLOR FILTER

This application claims priority from Japanese Patent Application No. JP2004-246428 filed on Aug. 26, 2004, which is incorporated hereinto by reference.

FIELD OF THE INVENTION

The present invention relates to a novel metal complex dye and a color toner and a color filter containing the dye.

BACKGROUND OF THE INVENTION

Dyes which are known as dyestuffs or pigments, are broadly employed in various uses, such as dying material for fiber, coloring material for resin or paints, photograph, printing, copying machines, image forming material in a printer and light-absorbing material of a filter. Recently, there have been proposed a variety of image forming dyes used for hard color copy employing ink-jet recording, electrophotography, silver salt photography, thermal transfer recording and the like. Along with development of electronic imaging, demands for filter dyes for use in solid camera tubes or color liquid crystal televisions and dyes for use in photo-recording mediums employing semiconductor lasers have increased and the usable field of dyes has been expanded.

In color copiers or color laser printers employing an electrophotography system are used toners composed of coloring material dispersed in resin or toners composed of coloring material adhered onto the resin particle surface. Allowing coloring material to adhere onto the resin particle surface colors only the surface and renders it difficult to achieve sufficient coloring effects. Further, problems arise with the release of the coloring material from the surface such that charging behavior varies or the surface of a fixing roller is stained. Accordingly, there are broadly used toners in which coloring material is dispersed in the interior of the toner particle. Performance required in such toners includes color reproducibility, image transparency in over-head project (or OHP) and light fastness. JP-A No. 62-157051, 62-255956 and 6-118715 (hereinafter, the term, JP-A refers to Japanese patent Application Publication) disclosed toners in which pigments as coloring material were dispersed within the toner particle. While these toners are superior in light fastness, they are insoluble and easily coagulated, producing problems such as lowered transparency or varied hue. JP-A Nos. 3-276161, 2-207273 and 2-207274 disclosed toners using dyes as coloring material. While these toners exhibit high transparency and cause no variation in hue, there is problem in lightfastness.

Color filters require high transparency so that a so-called dying method using dyes for coloring has been conducted. For instance, a dyeable photosensitive material is coated on the substrate such as glass and subjected to pattern exposure corresponding to one filter color, then, unexposed areas are washed off in the development stage and the remaining pattern portion is dyed with a dye. The foregoing-operation is successively repeated for all filter colors to prepare a color filter. In this method, the use of dyes enhances transparency, leading to superior optical properties as a color filter. However, lightfastness and heat resistance are limited therein so that coloring material exhibiting various superior resistance properties and enhanced transparency has been desired. Organic pigments exhibiting superior lightfastness and heat resistance have been employed in place of dyes. However, color filters using pigments proved to be difficult to obtain optical properties achieved by dyes.

In dyes usable in the respective uses described above, the following properties are commonly desired to be provided. Thus, it is to exhibit preferred hue in color reproduction, to exhibit appropriate spectral absorption characteristics, to be superior in image fastness, such as lightfastness, moisture-resistance and chemical resistance, and to exhibit enhanced molar absorptivity.

SUMMARY OF THE INVENTION

Accordingly, it is an object of the invention to provide a dye exhibiting preferable hue and spectral absorption characteristics in color reproduction, superior image fastness such as lightfastness, heat resistance and moisture resistance and enhanced molar absorptivity; color toners and color filters by use thereof.

The foregoing object of the invention is accomplished by the following constitution.

Thus, one aspect of the invention is directed to a metal complex dye containing a dye as a ligand and represented by the following formula (1):

Formula (1)

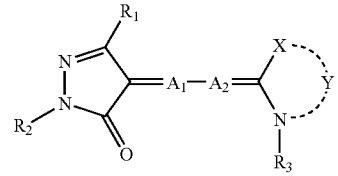

wherein $R_1$ represents an alkyl group, an aryl group, an alkoxy group, an alkoxycarbonyl group, an acyl group, an acyloxy group, an amido group, a carbamoyl group, an amino group, or cyano group; $R_2$ represents an alkyl group, an acyl group, a carbamoyl group or an alkoxycarbonyl group; $R_3$ represents an alkyl group, an alkenyl group or an aryl group, provided that the total number of carbon atoms of $R_1$ and $R_2$ is not less than 3; X represents —$CR_4R_5$—, —S—, —O— or —$NR_6$—, in which $R_4$ and $R_5$ represents a hydrogen atom, a halogen atom or a substituent, and $R_6$ represents a hydrogen atom or a substituent; Y represents an atomic group necessary to form a 5- or 6-membered ring; $A_1$ and $A_2$ are each a methine group which may be substituted.

Another aspect of the invention is directed to a color toner containing the metal complex dye described above.

Further, another aspect of the invention is directed to a color filter containing the metal complex dye described above.

According to the invention, there can be provided a metal complex dye exhibiting favorable color and superior lightfastness, a color toner exhibiting enhanced transparency in OHP images, and a color filter.

DETAILED DESCRIPTION OF THE INVENTION

Figure 1:
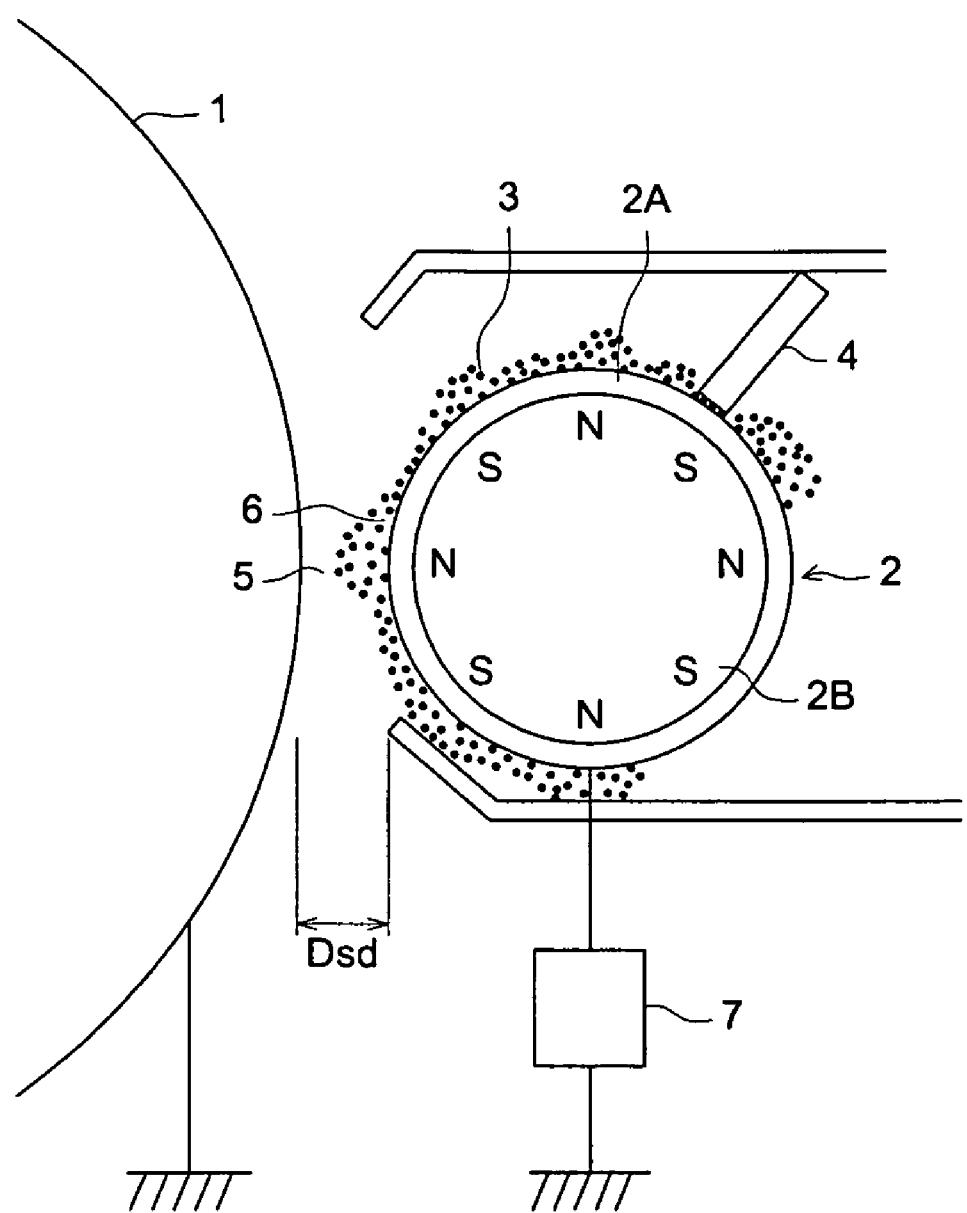
FIG. 1 illustrates an example of a non-contact development system.

The present invention has come into being as a result of extensive study of the problems described above. Thus, a metal complex dye containing a dye as a ligand of a specific structure represented by the foregoing formula (1) was discovered and it was found that a color toner and a color filter using the metal complex dye which exhibit superior color and image-fastness.

In the following, compounds of formulas (1) and (2) will be further described.

In formula (1), $R_1$ represents a substituted or substituted alkyl group, an aryl group, an alkoxy group, an alkoxycarbonyl group, an acyl group, an acyloxy group, an amido group, a carbamoyl group, an amino group, or cyano group.

Examples of an unsubstituted alkyl group include methyl, ethyl, propyl, isopropyl, tert-butyl, pentyl, hexyl, octyl, dodecyl, tridecyl, tetradecyl, and pentadecyl. A substituted alkyl group is, for example, trifluoromethyl. Examples of an aryl group include phenyl and naphthyl; example of an alkoxy group include methoxy, ethoxy, propyloxy, pentyloxy, hexyloxy, octyloxy and dodecyloxy; examples of an alkoxycarbonyl group include methyloxycarbonyl, ethyloxycarbonyl, butyloxycarbonyl, octyloxycarbonyl, and dodecyloxycarbonyl; examples of an acyl group include acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl; examples of an acyloxy group include acetyloxy, ethylcarbonyloxy, butylcarbonyloxy, octylcarbonyloxy, dodecylcarbonyloxy, and phenylcarbonyloxy; examples of an amido group include methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, doecylcarbonylamino, phenylcarbonylamino, and naphthylcarbonylamino; examples of a carbamoyl group include aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl and 2-pyridylaminocarbonyl; examples of an amino group amino, ethylamino, dimethylamino, butylamino, cyclopentylamino, 2-ethylhexylamino, dodecylamino, anilino, naphthylamine and 2-pyridylamino.

Of these groups, an alkyl group, trifluoromethyl group, alkoxycarbonyl group, an acyl group, a carbamoyl group and cyano group are preferred, and an alkyl group is more preferred. Of alkyl groups, a branched alkyl group is preferred and examples of a branched alkyl group include isopropyl, tert-butyl, isobutyl, sec-butyl, neo-pentyl and tert-amyl. of these, isopropyl and tert-butyl are more preferred. Increased bulkiness of $R_1$ results in enhanced lightfastness.

$R_2$ represents an alkyl group, an acyl group, a carbamoyl group or an alkoxycarbonyl group. Examples of an alkyl group include methyl, ethyl, propyl, isopropyl, tert-butyl, pentyl, hexyl, octyl, dodecyl, tridecyl, tetradecyl, and pentadecyl; examples of an acyl group include acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl; examples of a carbamoyl group include aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl and 2-pyridylaminocarbonyl; and examples of an alkoxycarbonyl group include methyloxycarbonyl, ethyloxycarbonyl, butyloxycarbonyl, octyloxycarbonyl, and dodecyloxycarbonyl.

$R_2$ of an alkyl group, an alkoxycarbonyl group, an acyl group or a carbamoyl group results in a dye exhibiting superior solubility in solvent and enhanced molar absorptivity. Specifically, $R_2$ is preferably an acyl group or a carbamoyl group.

The total number of carbon atoms of $R_1$ and $R_2$ is 3 or more. $R_1$ and $R_2$ is 3 or more results in enhanced solubility in solvent.

$R_3$ is an alkyl group, an alkenyl group or an aryl group. Examples of an alkyl group include methyl, ethyl, propyl, isopropyl, tert-butyl, pentyl, hexyl, octyl, dodecyl, tridecyl, tetradecyl, and pentadecyl; examples of an alkenyl group include phenyl and allyl; and examples of an aryl group include phenyl and naphthyl. $R_3$ is preferably an alkyl group, and of alkyl groups, methyl, ethyl, propyl, isopropyl, butyl, isobutyl, sec-butyl, pentyl and neo-pentyl are preferred; and methyl, ethyl, propyl, isopropyl and butyl are more preferred.

X is —$CR_4R_5$—, —S—, —O— or —$NR_6$—, and preferably —$CR_4R_5$—, —S—, or —O—, in which $R_4$ and $R_5$ is a hydrogen atom, a halogen atom or a substituent. Examples of a halogen atom include a fluorine atom, chlorine atom, a bromine atom and a iodine atom, and fluorine atom and a chlorine atom are preferred. The substituent is not specifically limited, including any one which is capable of being substituted.

Examples of such a substituent include an alkyl group (e.g., methyl, ethyl, propyl, isopropyl, tert-butyl, pentyl, hexyl, octyl, dodecyl, tridecyl, tetradecyl, pentadecyl), a cycloalkyl group (e.g., cyclopentyl, cyclohexyl), an alkenyl group (e.g., vinyl, allyl), an alkynyl group (e.g., ethynyl, propargyl), an aryl group (e.g., phenyl. naphthyl), a heteroallyl group (e.g., furyl, thienyl, pyridyl, pyridazyl, pyrimidyl, pyrazyl, triazyl, imidazolyl, pyrazolyl, thiazolyl, benzoimidazolyl, benzooxazolyl, quinazolyl, phthalazyl), a heterocyclic group (e.g., pyrrolidyl, imidazolidyl, morpholyl group, oxazolidyl), an alkoxy group (e.g., methoxy, ethoxy, propyloxy, pentyloxy, hexyloxy, octyloxy, dodecyloxy), a cycloalkoxy group (e.g., cyclopentyloxy, cyclohexyloxy), an aryloxy group (e.g., phenoxy, naphthyloxy), an alkylthio group (e.g., methylthio, ethylthio, propylthio, pentylthio, hexylthio, octylthio, dodecylthio), a cycloalkylthio group (e.g., cyclopentylthio, cyclohexylthio), an arylthio group (e.g., phenylthio, naphthylthio), an alkoxycarbonyl group (e.g., methyloxycarbonyl, ethyloxycarbonyl, butyloxycarbonyl, octyloxycarbonyl, dodecyloxycarbonyl), an aryloxycarbonyl group (e.g., phenyloxycarbonyl, naphthyloxycarbonyl), a sulfamoyl group (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, 2-pyridylaminosulfonyl), an acyl group (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, pyridylcarbonyl), an acyloxy group (e.g., acetyloxy, ethylcarbonyloxy, butylcarbonyloxy, octylcarbonyloxy, dodecylcarbonyloxy, phenylcarbonyloxy), an amido group (e.g., methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, naphthylcarbonylamino), a carbamoyl group (e.g., aminocarbony, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, 2-pyridylaminocarbonyl), a ureido group (e.g., methylureido, ethylureido, pentylureido, cyclohexylureido, octylureido, dodecylureido, phenylureido, naphthylureido, 2-pyridylureido), a sulfinyl group (e.g., methylsulfinyl, ethylsulfinyl, butylsulfinyl, cyclohexylsulfinyl, 2-ethylhexylsulfinyl, dodecysulfinyl, phenylsulfinyl, naphthylsulfinyl, 2-pyridylsulfinyl), an alkylsulfonyl group (e.g., methylsulfinyl, ethylsulfinyl, butylsulfinyl, cyclohexylsulfinyl, 2-ethylhexylsulfinyl, dodecylsulfinyl), an arylsulfonyl group (e.g., phenylsulfonyl, naphthylsulfonyl, 2-pyridylsulfonyl), an amino group (e.g., amino, ethylamino, dimethylamino, butylamino, cyclopentylamino, 2-ethylhexylamino, dodecylamino, anilino, naphthylamine, 2-pyridylamino), cyano group and nitro group.

Of the foregoing, $R_4$ and $R_5$ are each preferably a hydrogen atom, an alkyl group or an aryl group, and more preferably a hydrogen atom or an alkyl group. Of alkyl group, methyl, ethyl, propyl, isopropyl, butyl, isobutyl, sec-butyl and neo-pentyl are preferred, and methyl is more preferred.

$R_6$ is a hydrogen atom or a substituent. Examples of the substituent include those as cited in the foregoing $R_4$ and $R_5$. $R_6$ is preferably a hydrogen atom, an alkyl group or an aryl group, and more preferably a hydrogen atom or an alkyl group. Of alkyl groups, methyl, ethyl, propyl, isopropyl, butyl, isobutyl, sec-butyl, pentyl and neo-pentyl are preferred and methyl and ethyl are more preferred.

Y is an atomic group necessary to form a 5- or 6-membered ring and preferably an atomic group necessary to form a 5-membered ring, for examples, —$CR_7$=$CR_8$— and —$CR_9R_{10}$—$CR_{11}R_{12}$—, in which $R_7$ to $R_{12}$ are each a hydrogen atom, a halogen atom or a substituent, and $R_7$ and $R_8$ or $R_9$ and $R_{10}$ may combine with each other to form a ring. The halogen atom is a fluorine, chlorine, bromine or iodine atom, and a fluorine or chlorine atom is preferred. Examples of the substituent are those as cited in the foregoing $R_4$ and $R_5$. Of those, an alkyl group and aryl group are preferred and an alkyl group is more preferred. $R_7$ to $R_{12}$ are each most preferably a hydrogen atom or methyl. $R_7$ and $R_8$ or $R_9$ and $R_{10}$ may combine with each other to form a ring, such as a cyclopentane ring, cyclohexane ring, a benzene ring, pyridine ring or a naphthalene ring a benzene ring is preferred, which mat be substituted.

$A_1$ and $A_2$ are each a methine group, which may be substituted, and examples of a substituent are those as cited in the foregoing $R_4$ and $R_5$. Such a substituent is preferably an alkyl group, aryl group, aralkyl group, alkoxy group, aryloxy group or a heterocyclic group. Thus, $A_1$ and $A_2$ are preferably an unsubstituted, or alkyl- or alkoxy substituted methine group, and more preferably an unsubstituted methine group.

The compound of formula (1) is preferably represented by the following formulas (1a) to (1d):

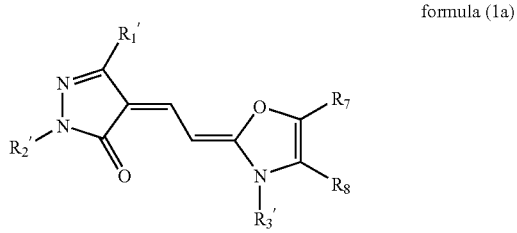

formula (1a)

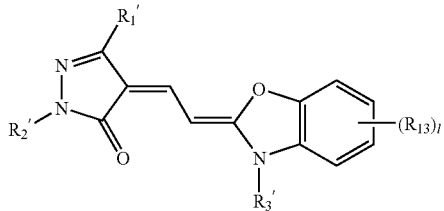

formula (1b)

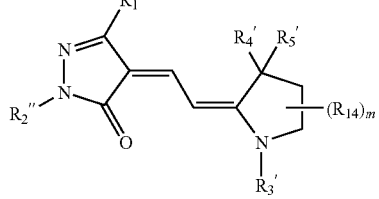

formula (1c)

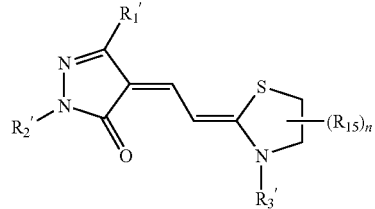

formula (1d)

In the foregoing formula (1a), $R_1'$ is an alkyl group, e.g., methyl, ethyl, propyl, isopropyl, butyl, tert-butyl, pentyl, hexyl, octyl, dodecyl, tridecyl, tetradecyl and pentadecyl, and is preferably a branched alkyl group. The branched alkyl group is, for example, isopropyl, tert-butyl, isobutyl, sec-butyl, neo-pentyl or tert-amyl, and of these, isopropyl or tert-butyl is more preferred.

$R_2'$ is an alkyl group, an acyl group or a carbamoyl group, and preferably an acyl group or a carbamoyl group. Examples of an alkyl group include methyl, ethyl, propyl, isopropyl, tert-butyl, pentyl hexyl, octyl, dodecyl, tridecyl, tetradecyl and pentadecyl; examples of an acyl group include acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl; examples of a carbamoyl group include aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl and pyridylaminocarbonyl. Of alkyl groups, methyl, ethyl, propyl, isopropyl, butyl and tert-butyl are preferred. Of acyl groups, acetyl, ethylcarbonyl, propylcarbonyl, butylcarbonyl and isobutylcarbonyl are preferred, and acetyl or isobutylcarbonyl is more preferred. The total number of carbon atoms of $R_1'$ and $R_2'$ is 3 or more.

$R_3'$ is an alkyl group, an alkenyl group or aryl group. Examples of an alkyl group include methyl, ethyl, propyl, isopropyl, tert-butyl, pentyl hexyl, octyl, dodecyl, tridecyl, tetradecyl and pentadecyl; examples of an alkenyl group include vinyl and allyl; examples of an aryl group include phenyl and naphthyl. $R_3'$ is preferably an alkyl group, more preferably, methyl, ethyl, propyl, isopropyl, butyl, isobutyl, sec-butyl, pentyl or neo-pentyl, and still more preferably methyl, ethyl, propyl, isopropyl or butyl.

$R_7$ and $R_8$ are each a hydrogen atom, a halogen atom, or a substituent, and preferably a hydrogen atom or a substituent, provided that $R_7$ and $R_8$ may combine with each other to form a ring. The halogen atom is a fluorine atom, a chlorine atom, bromine atom or an iodine atom, and preferably a fluorine atom or a chlorine atom. Examples of the substituent include those as cited in the foregoing $R_4$ and $R_5$, of which an alkyl group and aryl group are preferred, and an alkyl group is more preferred. Of alkyl groups, methyl, ethyl, propyl, isopropyl, butyl, isobutyl, sec-butyl, pentyl, and neo-pentyl are preferred and methyl is most preferred. $R_7$ and $R_8$ may combine with each other to form a 5- or 6-membered ring, e.g., a cyclopentane ring, cyclohexane ring, benzene ring, pyridine ring and naphthalene ring.

In formula (1b), $R_1'$, $R_2'$ and $R_3'$ are respectively the same as defined in $R_1'$, $R_2'$ and $R_3'$ of the foregoing formula (1a). $R_{13}$ is a halogen atom or a substituent. Examples of a halogen atom include a fluorine atom, chlorine atom, bromine atom or an iodine atom, and preferably a fluorine atom or a chlorine atom. Examples of a substituent include those as cited in the foregoing $R_4$ and $R_5$. The substituent is preferably an alkyl group, an alkoxy group, an alkylthio group, an alkoxycarbonyl group, a sulfamoyl group, an acyl group, an acyloxy group, an amide group, carbamoyl group, an amino group, cyano group or nitro group, and more preferably an alkyl group. Of the alkyl group, methyl, ethyl, propyl, isopropyl, butyl, isobutyl, sec-butyl, pentyl or neo-pentyl is more preferred, and methyl is still more preferred. Designation "1" is an integer of 0 to 4. When 1 is 2 or more, plural $R_{13}$s may be the same or different.

In formula (1c), $R_3'$ is the same as $R_3'$ of the foregoing formula (1a). $R_1''$ is trifluoromethyl, an alkoxycarbonyl group, an acyl group, a carbamoyl group or cyano group. Examples of an alkoxycarbonyl group include methyloxycarbonyl, ethyloxycarbonyl, butyloxycarbonyl, octyloxycarbonyl and dodecyloxycarbonyl; examples of an acyl group include acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl and pyridylcarbonyl; and examples of a carbamoyl group include aminocarbony, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl and 2-pyridylaminocarbonyl. Of the foregoing, trifluoromethyl, an alkoxycarbonyl group and cyano group are preferred. Of the alkoxycarbonyl group, methyloxycarbonyl orethyloxycarbonyl is preferred.

$R_2''$ is an alkyl group, an acyl group or a carbamoyl group, and preferably an acyl group or a carbamoyl group. Examples of an alkyl group-include methyl ethyl, propyl, isopropyl, tert-butyl, pentyl, hexyl, octyl, dodecyl, tridecyl, tetradecyl and pentadecyl; examples of an acyl group include acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl and pyridylcarbonyl; and examples of a carbamoyl group include aminocarbony, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl and 2-pyridylaminocarbonyl. Of the foregoing, an alkyl group or acyl group is preferred. Of the alkyl group, methyl, ethyl, propyl, isopropyl, butyl or tert-butyl is preferred, and methyl is still more preferred. Of the acyl group, acetyl, ethylcarbonyl, propylcarbonyl, butylcarbonyl or isobutylcarbonyl is preferred, and acetyl or isobutylcarbonyl is more preferred. The total number of carbon atoms of $R_1''$ and $R_2''$ is 3 or more.

$R_4'$ and $R_5'$ are each a hydrogen atom, a halogen atom or a substituent; $R_{14}$ is a halogen atom or a substituent; and m is an integer of 0 to 4. $R_4'$ and $R_5'$ are respectively the same as $R_4$ and $R_5$ of the foregoing formula (1), and preferably a hydrogen atom or an alkyl group. Of the alkyl group, methyl, ethyl, propyl, isopropyl, butyl, isobutyl, sec-butyl, pentyl or neo-pentyl is preferred and methyl or ethyl is more preferred.

$R_{14}$ is the same as $R_{13}$ of the foregoing formula (1b), and preferably an alkyl group. Of the alkyl group, methyl, ethyl, propyl, isopropyl, butyl, isobutyl, sec-butyl, pentyl or neo-pentyl is preferred, and methyl or ethyl is more preferred.

Designation "m" is an integer of 0 to 4, and when m is 2 or more, plural $R_{14}$s may be the same or different. $R_4'$, $R_5'$ and $R_{14}$ which are attached to adjacent carbon atoms, may combine with each other to form a ring.

In formula (1d), $R_1'$, $R_2'$ and $R_3'$ are the same as defined in $R_1'$, $R_2'$ and $R_3'$ of formula (1a). $R_{15}$ is a halogen atom or a substituent. $R_{15}$ is also the same as $R_{13}$ of the foregoing formula (1b) and preferably a hydrogen atom or an alkyl group. Of the alkyl group, methyl, ethyl, propyl, isopropyl, butyl, isobutyl, sec-butyl, pentyl or neo-pentyl is preferred and methyl or ethyl is more preferred.

Designation "n" is an integer of 0 to 4, and when n is 2 or more, plural $R_{15}$s may be the same or different. $R_{15}$s which are attached to adjacent carbon atoms, may combine with each other to form a ring.

The combination of $R_1$, X and Y is greatly important in color reproduction, and in the combination of dyes of the foregoing formulas (1a), (1b), (1c) and (1d), more superior color reproduction can be achieved.

Specific examples of the dye represented by formula (1) are shown below but the invention is not limited to these.

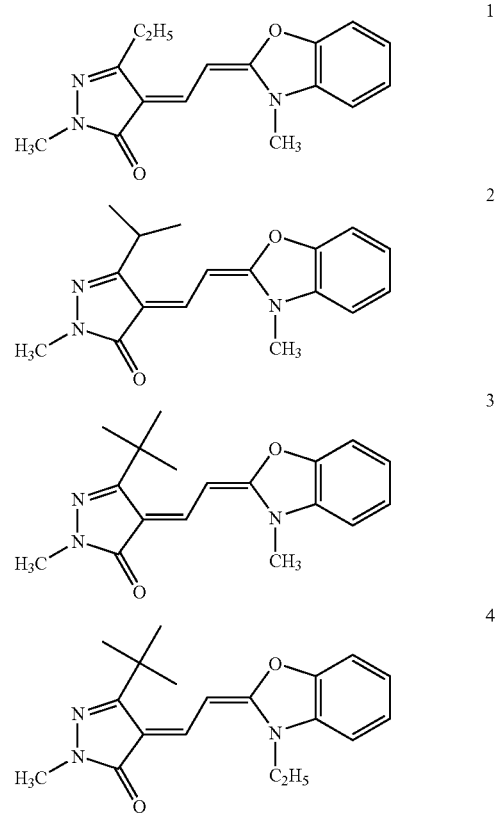

-continued
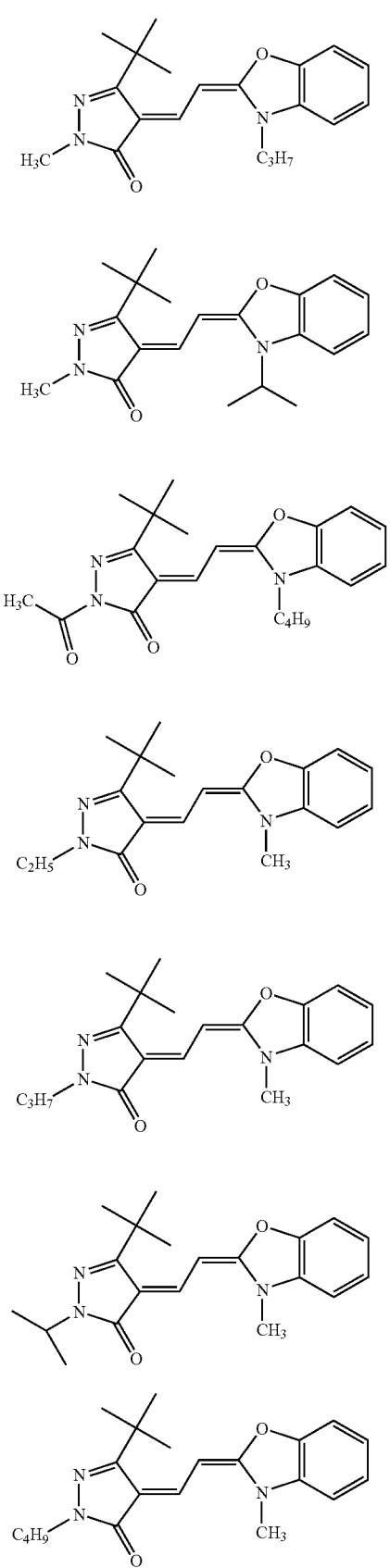
-continued
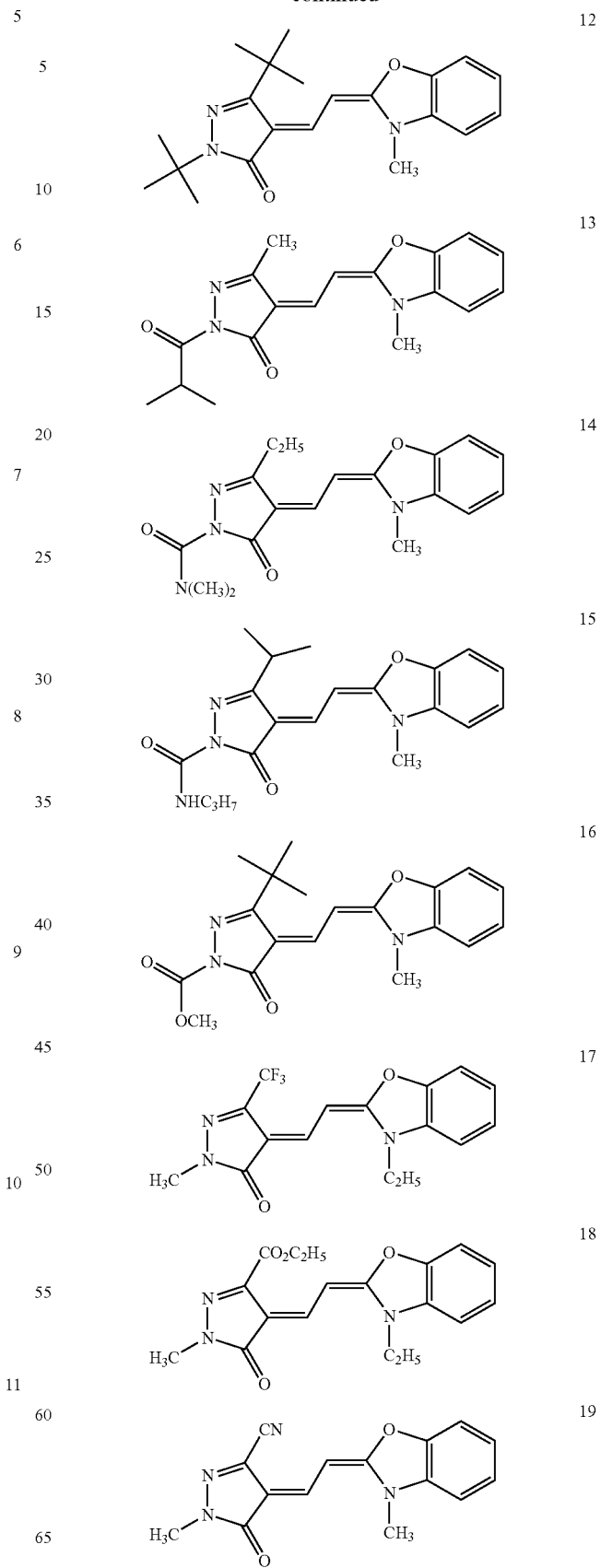

20
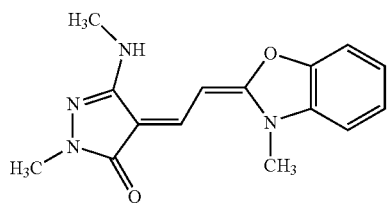
21
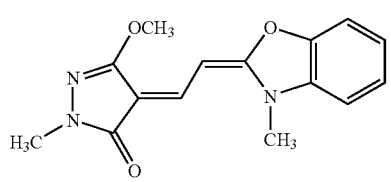
22
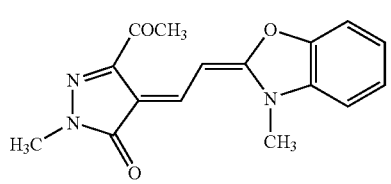
23
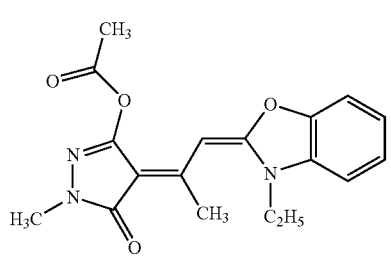
24
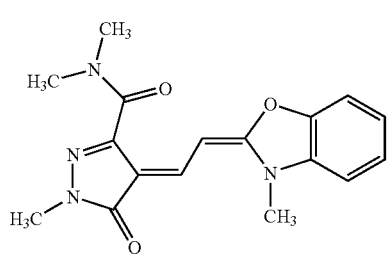
25
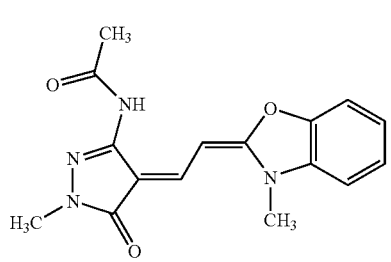
26
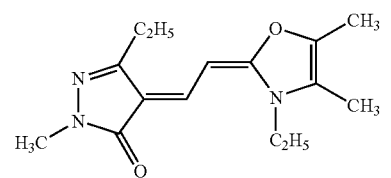
27
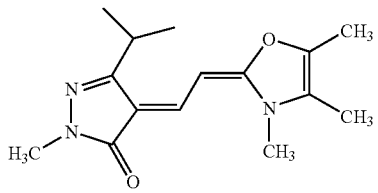
28
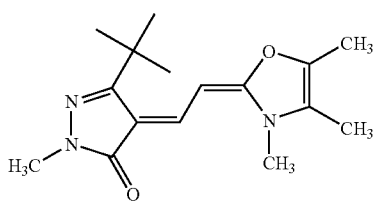
29
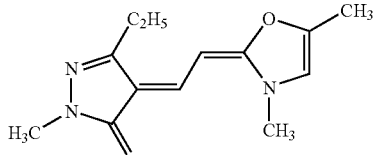
30
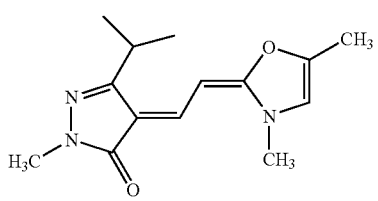
31
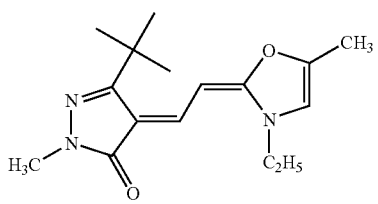
32
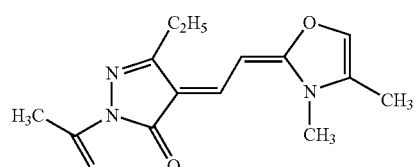
33
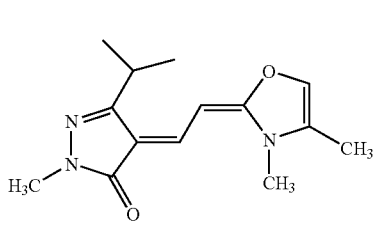
34
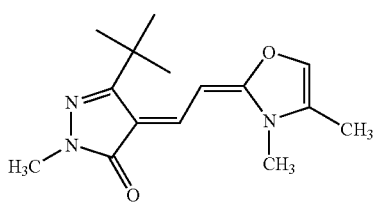

-continued
| | |
|---|---|
| 35 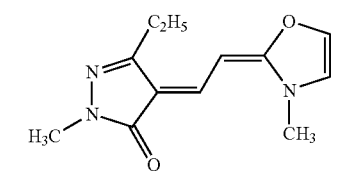 | 43 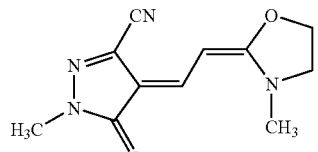 |
| 36 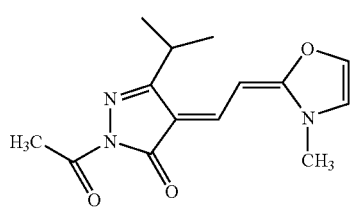 | 44 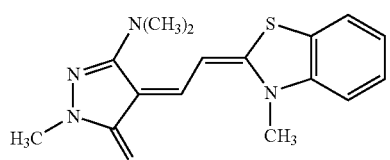 |
| 37 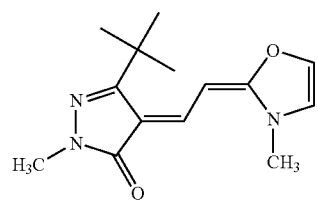 | 45 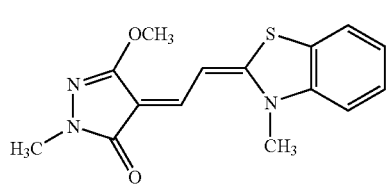 |
| 38 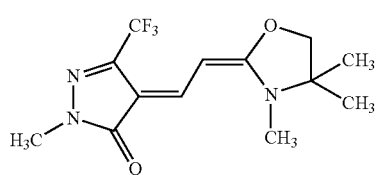 | 46 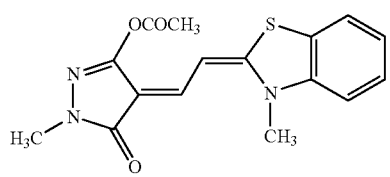 |
| 39 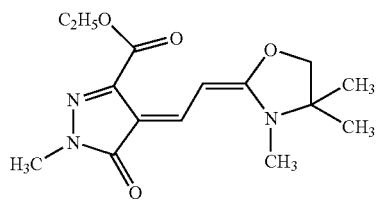 | 47 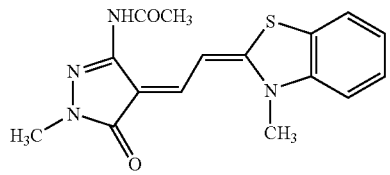 |
| 40 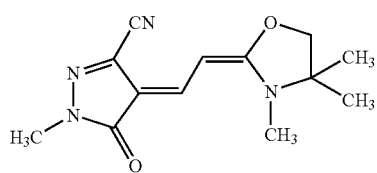 | 48 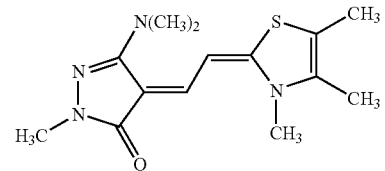 |
| 41 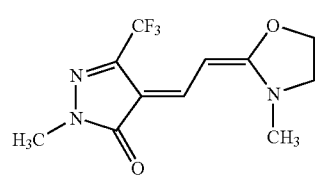 | 49 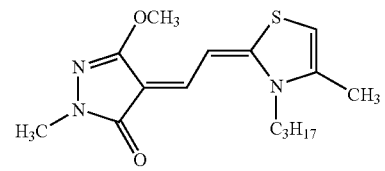 |
| 42 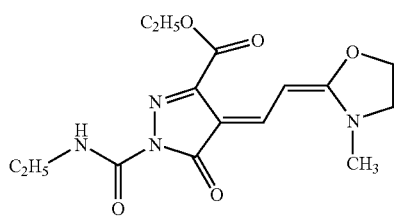 | 50 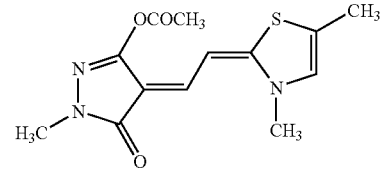 |
| | 51  |

-continued
52
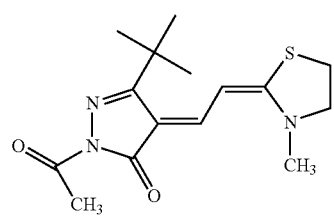
53
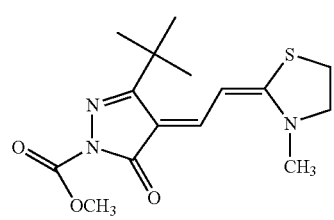
54
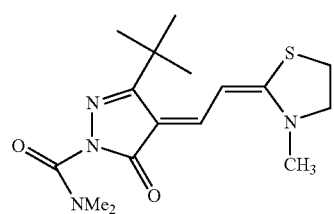
55
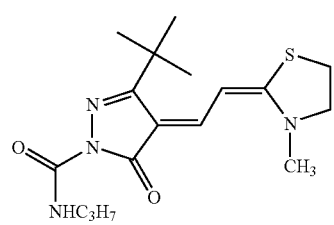
56
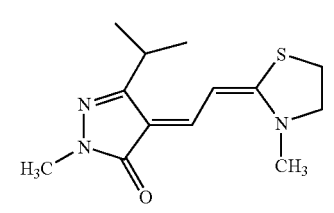
57
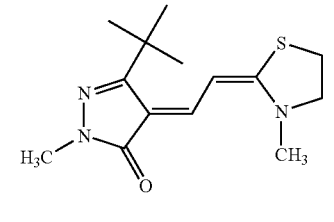
58
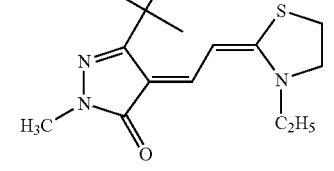
-continued
59
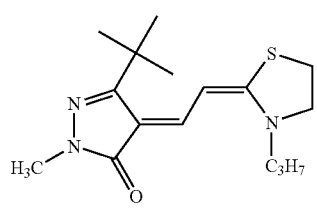
60
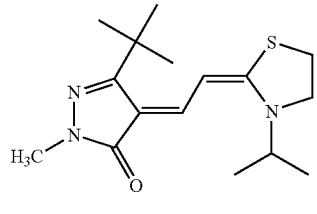
61
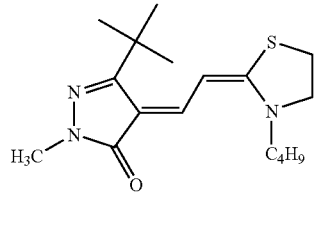
62
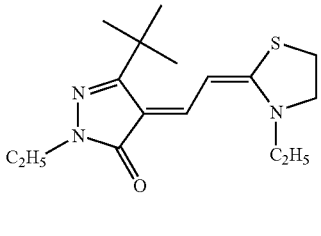
63
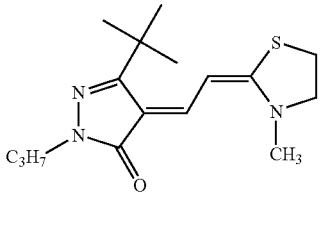
64
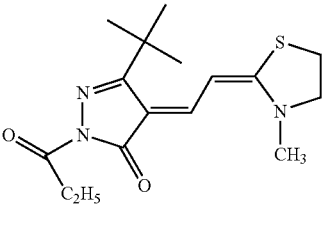
65
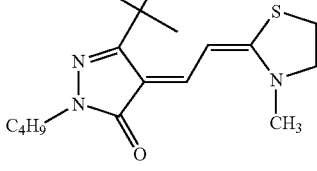

-continued
66
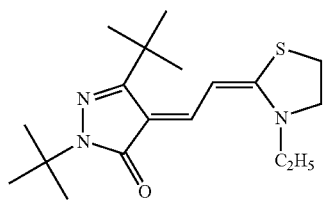
67
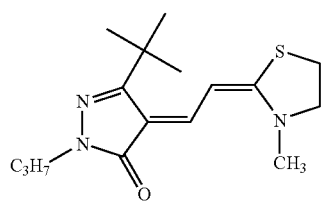
68
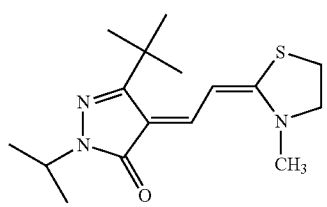
69
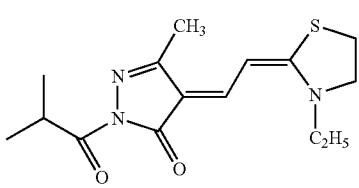
70
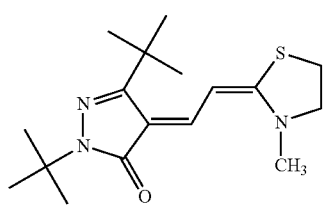
71
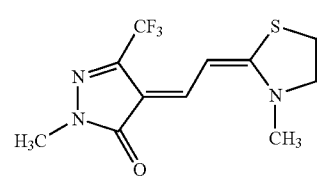
72
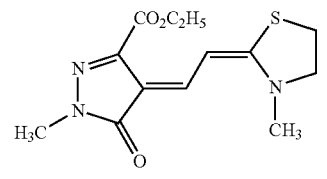
73
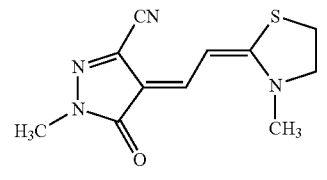
-continued
74
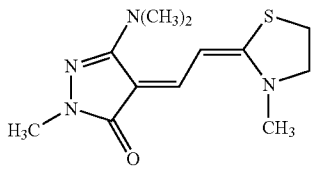
75
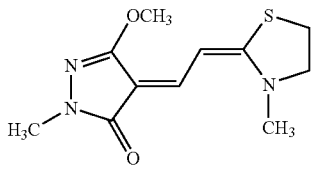
76
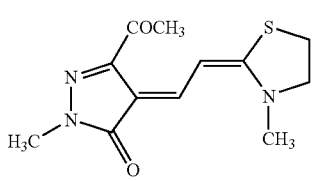
77
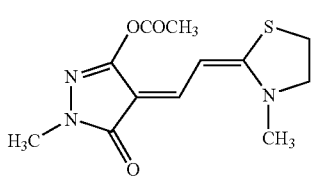
78
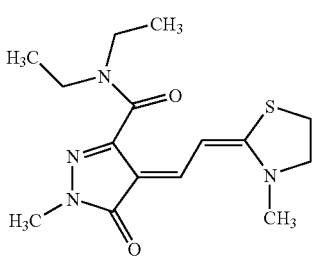
79
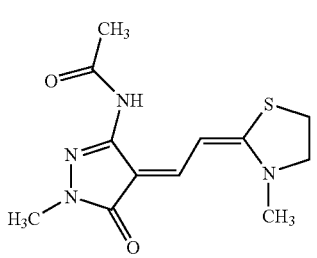
80
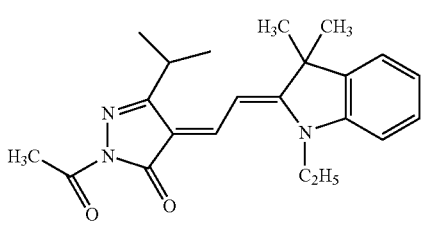

-continued
81
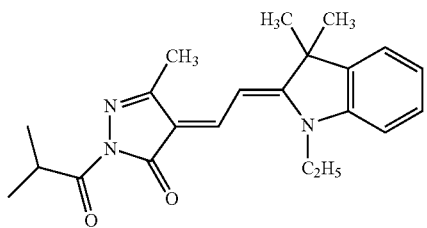
82
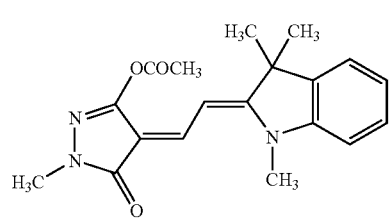
83
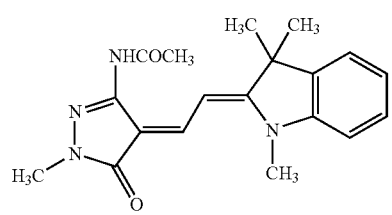
84
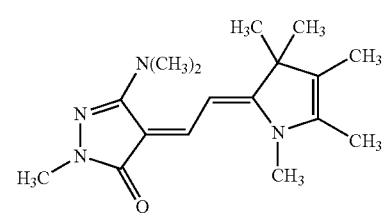
85
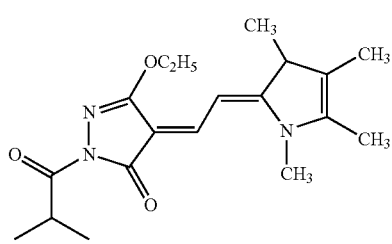
86
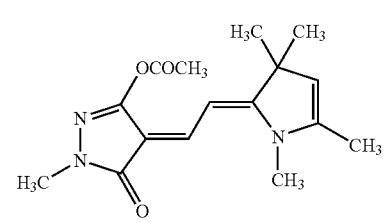
87
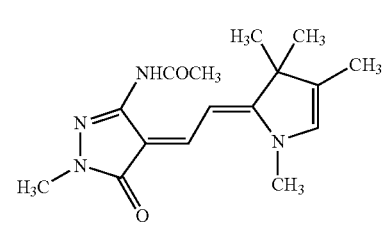
-continued
88
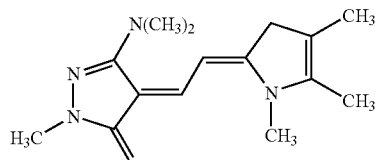
89
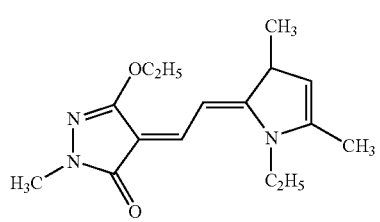
90
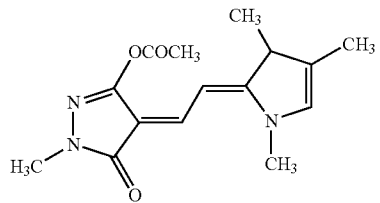
91
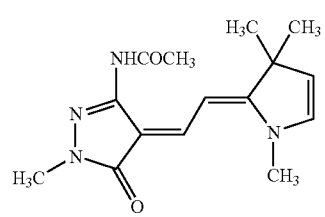
92
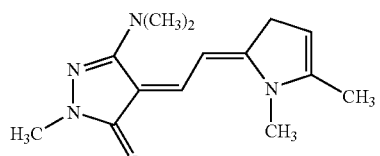
93
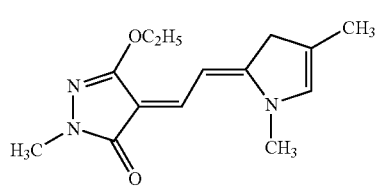
94
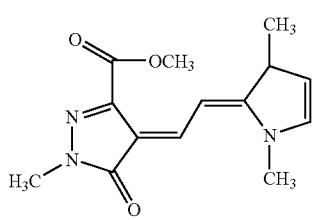
95

-continued
96 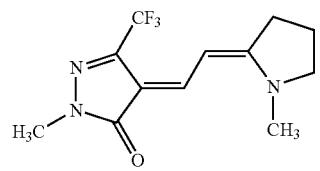
97 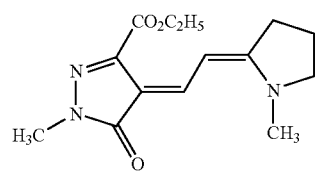
98 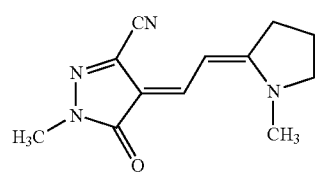
99 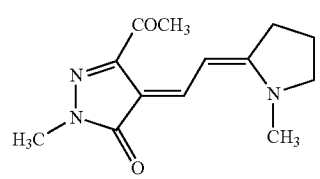
100 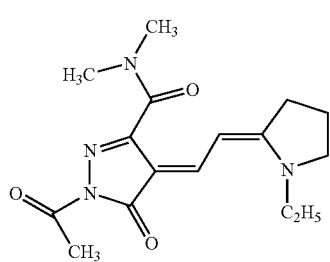
101 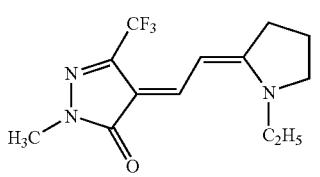
102 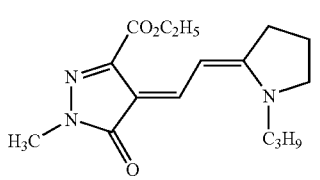
103 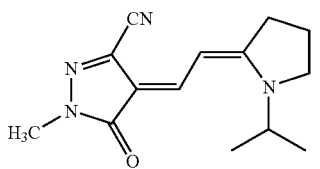
-continued
104 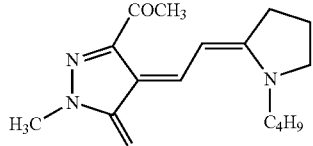
105 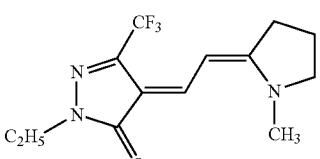
106 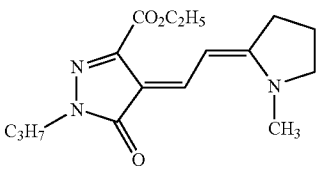
107 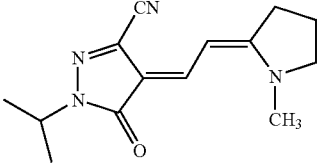
108 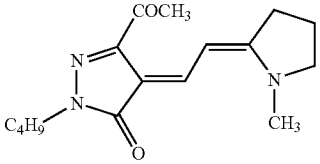
109 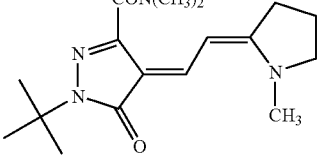
110 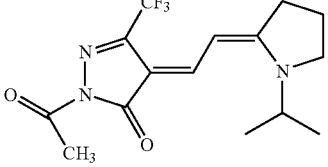
111 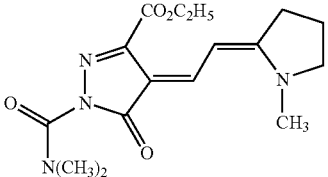
112 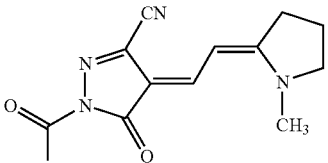

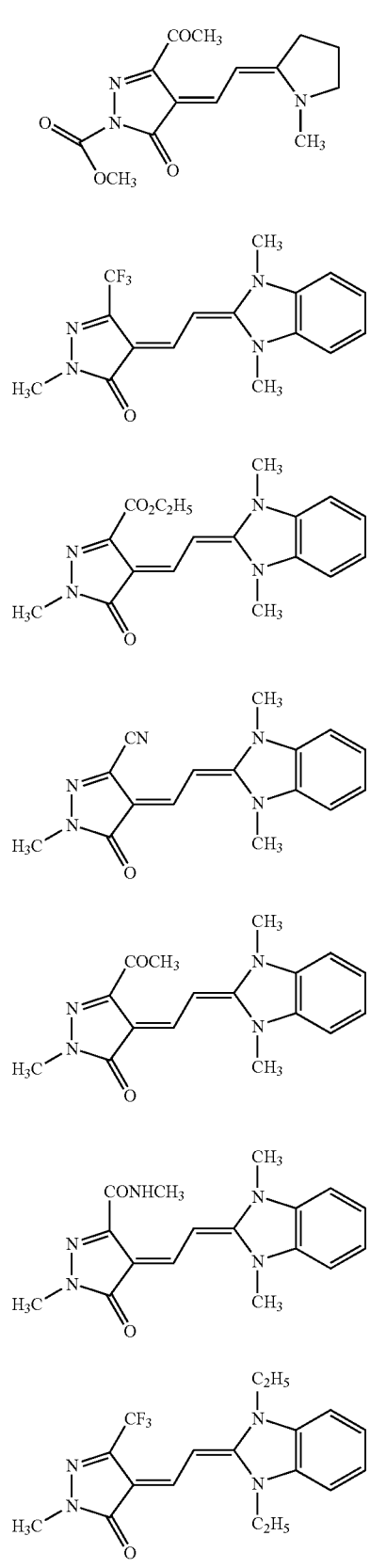
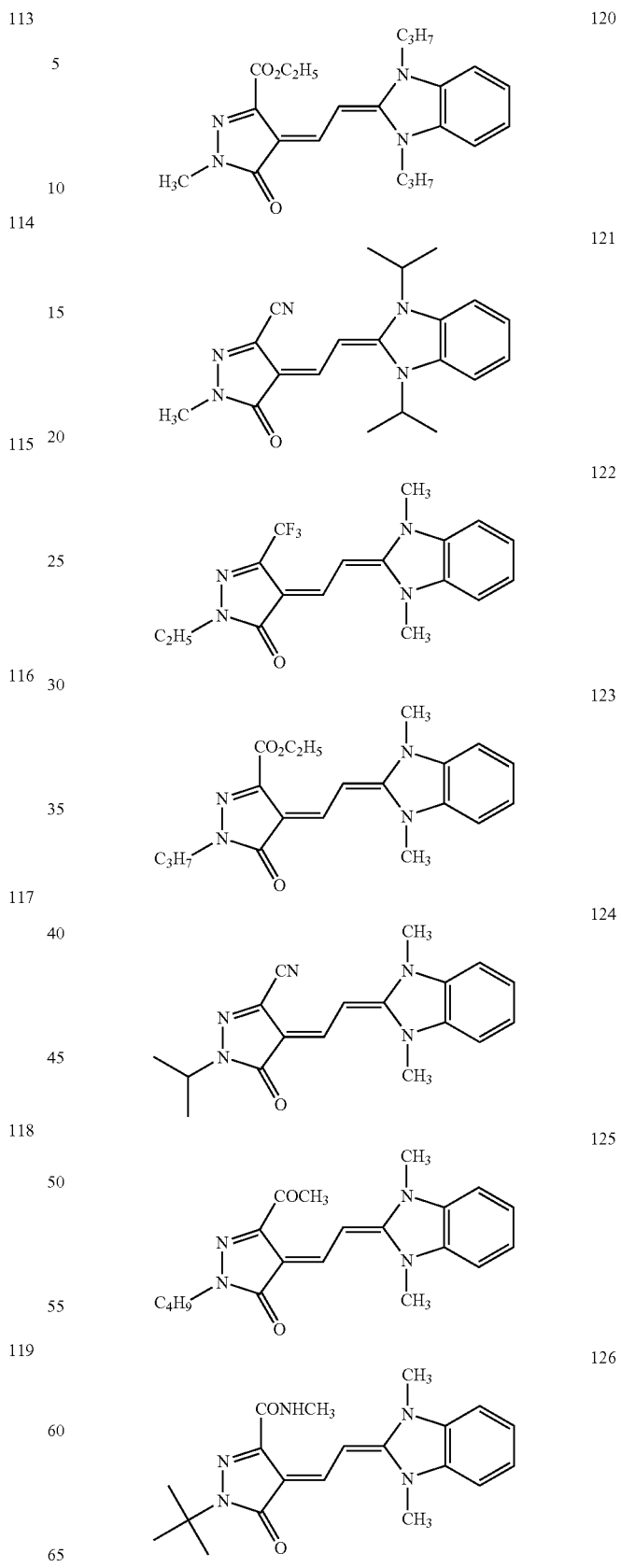

-continued
127 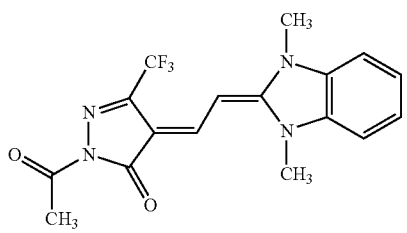
128 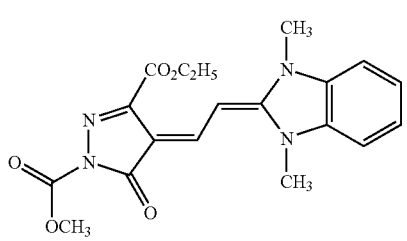
129 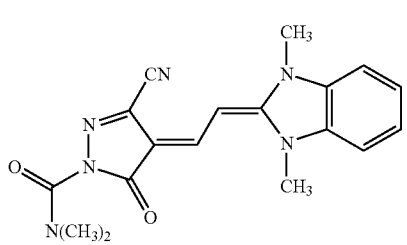
130 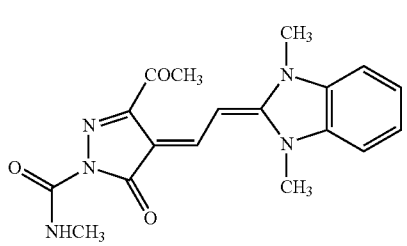
131 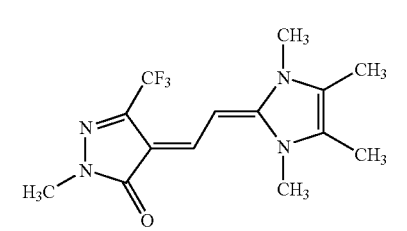
132 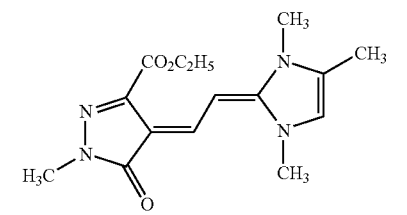
133 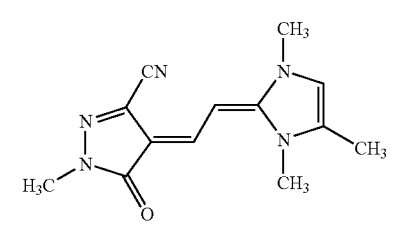
-continued
134 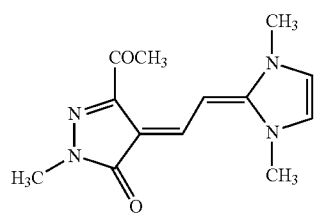
135 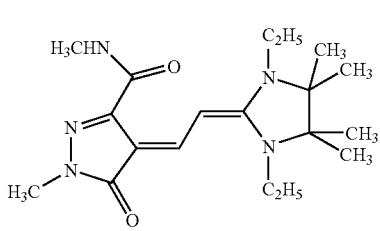
136 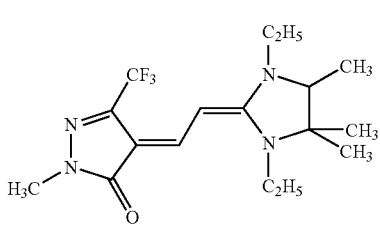
137 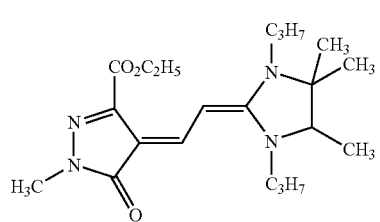
138 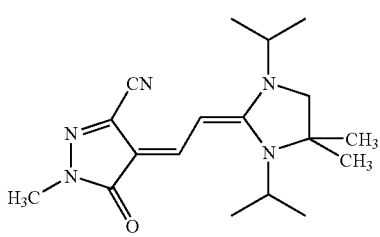
139 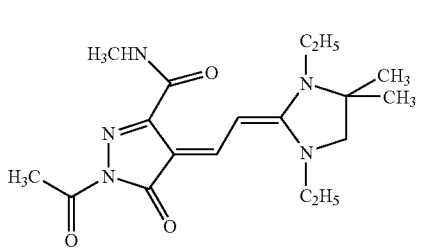
140 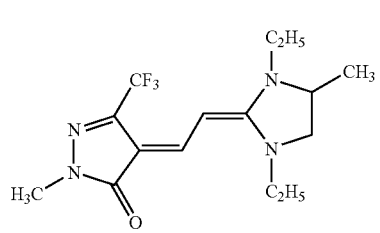

141
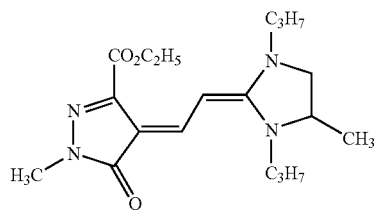

142
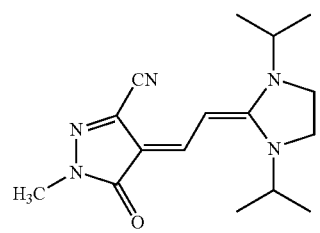

143
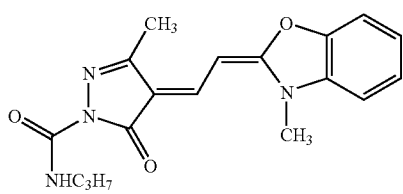

144
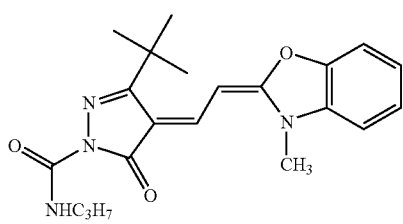

145
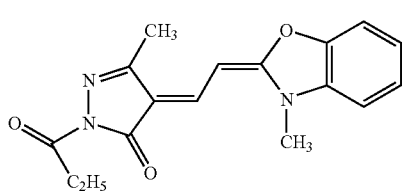

146
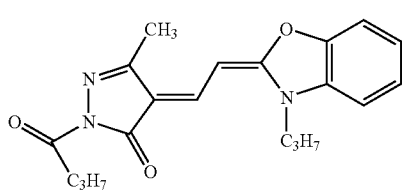

147
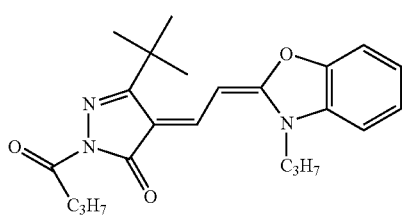

148
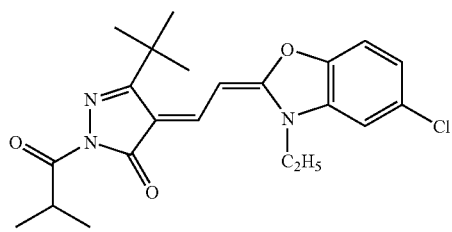

149
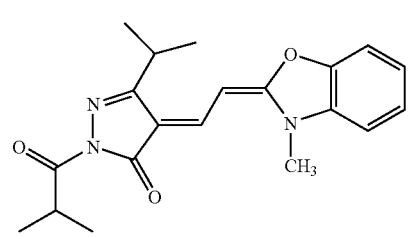

150
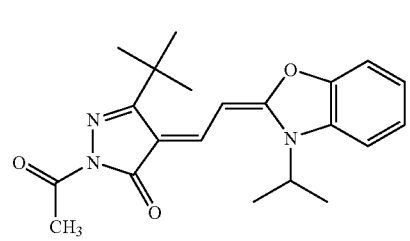

151
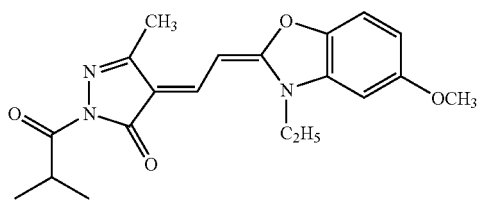

152
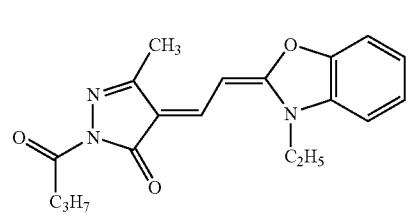

The compounds of formula (1) can be synthesized in accordance with conventionally known methods as described in JP-A Nos. 6-301136 and 10-60296 and "The Cyanine Dyes and Related Compounds", F. Hamer, Interscience Publishers, 1964. Metal complex dyes can be synthesized with reference to conventionally known methods described in JP-A No. 2000-191934.

Specific examples of synthesis of the compounds of formula (1) are shown below, but other compounds can be synthesized similarly, and the synthesis methods are not limited to these.

Synthesis Example 1

Synthesis of Exemplified Compound 3

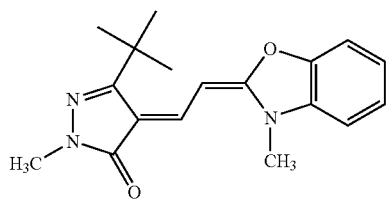

To 300 ml of ethanol were added 7.71 g of 3-tert-butyl-1-methyl-5-pyrazolone, 21.01 g of 2-[2-(acetyl-phenyl-amino)-vinyl]-3-methylbenzoxazole-3-nium; iodide and 10.01 g of triethylamine and heated at approximately 80° C. for 3 hr. to perform reaction. After completing the reaction, ethanol and triethylamine were removed under reduced pressure. The obtained residue was recrystallized in acetonitrile to obtain 6.79 g of exemplified compound 3. According to analysis of 1H-NMR and MASS spectrum of the thus obtained solid, exemplified compound 3 was identified.

Synthesis Example 2

Synthesis of Exemplified Compound 13

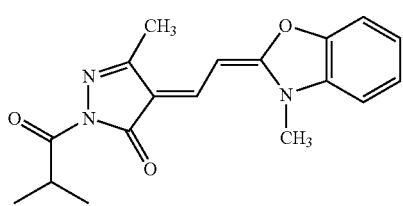

To 300 ml of ethanol were added 8.41 g of 3-tert-butyl-1-isopropanoyl-5-pyrazolone, 21.01 g of 2-[2-(acetyl-phenyl-amino)-vinyl]-3-methylbenzoxazole-3-nium; iodide and 10.01 g of triethylamine and heated at approximately 80° C. for 3 hr. to perform reaction. After completing the reaction, ethanol and triethylamine were removed under reduced pressure. The obtained residue was recrystallized in acetonitrile to obtain 9.09 g of exemplified compound 13. According to analysis of 1H-NMR and MASS spectrum of the thus obtained solid, exemplified compound 13 was identified.

Synthesis Example 3

Synthesis of Exemplified Compound 28

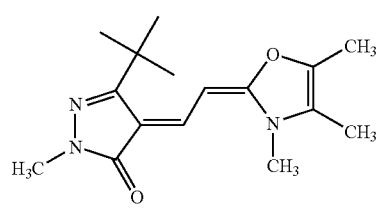

To 300 ml of ethanol were added 7.71 g of 3-tert-butyl-1-methyl-5-pyrazolone, 19.91 g of 2-[2-(acetyl-phenyl-amino)-vinyl]-3,4,5-trimethylbenzoxazole-3-nium; iodide and 10.01 g of triethylamine and heated at approximately 80° C. for 3 hr. to perform reaction. After completing the reaction, ethanol and triethylamine were removed under reduced pressure. The obtained residue was recrystallized in acetonitrile to obtain 6.51 g of exemplified compound 28. According to analysis of 1H-NMR and MASS spectrum of the thus obtained solid, exemplified compound 3 was identified.

Synthesis Example 4

Synthesis of Exemplified Compound 57

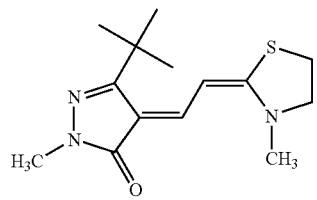

To 300 ml of ethanol were added 7.71 g of 3-tert-butyl-1-methyl-5-pyrazolone, 19.41 g of 2-[2-(acetyl-phenyl-amino)-vinyl]-3-methyl-4,5-dihydro-thiazole-3-nium; iodide and 10.01 g of triethylamine and heated at approximately 80° C. for 3 hr. to perform reaction. After completing the reaction, ethanol and triethylamine were removed under reduced pressure. The obtained residue was recrystallized in acetonitrile to obtain 4.75 g of exemplified compound 3. According to analysis of 1H-NMR and MASS spectrum of the thus obtained solid, exemplified compound 57 was identified.

Synthesis Example 5

Synthesis of Exemplified Compound 97

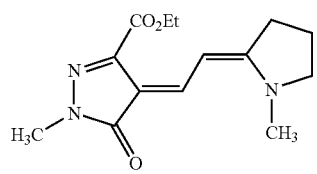

To 100 ml of pyridine were added 10.51 g of 3-carboxylic-acid-ester-1-methyl-5-pyrazolone, 16.41 g of 1-methyl-5-(2-phenylamino-vinyl)-3,4-dihydro-pyrrolenium, iodide, 5.01 g of triethylamine and 5.10 g of acetic anhydride and heated at approximately 80° C. for 3 hr. to perform reaction. After completing the reaction, pyridine and trietylamine were removed under reduced pressure. The obtained residue was recrystallized in acetonitrile to obtain 6.41 g of exemplified compound 97. According to analysis of 1H-NMR and MASS spectrum of the thus obtained solid, exemplified compound 97 was identified.

Synthesis Example 6

Synthesis of Exemplified Compound 115

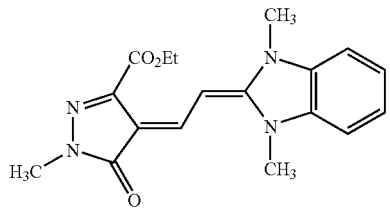

To 100 ml of pyridine were added 10.51 g of 3-carboxylic-acid-ester-1-methyl-5-pyrazolone, 19.56 g of 1,3-dimethyl-2-(2-phenylamino-vinyl)-benzoimidazole-1-nium; iodide, 5.01 g of triethylamine and 5.10 g of acetic anhydride and heated at approximately 80° C. for 3 hr. to perform reaction. After completing the reaction, pyridine and trietylamine were removed under reduced pressure. The obtained residue was recrystallized in acetonitrile to obtain 11.16 g of exemplified compound 115. According to analysis of 1H-NMR and MASS spectrum of the thus obtained solid, exemplified compound 115 was identified.

In the metal complex dye of the invention, the metal atom is selected from atoms of from Sc to Zn in the 4th period of the periodical table, atoms of from Y to Cd in the 5th period and atoms of from La to Hg in the 6th period, preferably Mn, Fe, Co, Ni, Cu, Zn, Ru, Fe, or Ti, and more preferably Ni, Cu or Zn.

In the metal complex dye of the invention, ligands other than the compounds of formula (1) are those described in JP-A Nos. 2000-251957, 2000-311723, 2000-323191, 2001-6760, 2001-59062 and 2001-60467. Specific examples thereof include a halide ion, hydroxyl ion, ammonia, pyridine, an amine (e.g., methylamine, diethylamine, tributylamine), cyanide ion, cyanate ion, thilate ion, thiocynate ion, and various chelate ligands such as pyridines, aminopolycarboxylic acids and 8-hydroxyquinolines. Chelate ligands are exemplified in Keihei Ueno "Chelate Kagaku".

Preferred bidentate ligand are ligands which are coordinated with an acyloxy group, an oxalylene group, an acylthio group, an thioacyloxy group, thiacylthio group, an acylaminooxy group, a thiocarbamate group, a dithiocarbamate group, a thiocarbonate group, a dithiocarbonate group, a trithiocarbonate group, an alkylthio group or an arylthio group, or a ligand composed of a dialkylketone or a carbonamide.

Preferred unidentate ligand are ligands which are coordinated with an acyl group, a carbonyl group, a thiocyanate group, an isothiocyanate group, a cyanate group, an isocyanate group, a halogenatom, cyano group, an alkylthio group, an arylthio group, an alkoxy group, or anaryloxy, or a ligand composed of dialkylketone or carbonamide.

Specific examples are shown below but are not limited to these. The structure shown below is only one canonical structure of possible resonance structures, in which distinction of a covalent bond (designated as —) and coordination bond (designated as . . . ) is simply formal and not absolute distinction.

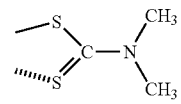

X-1

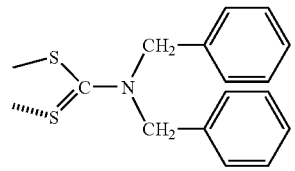

X-2

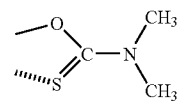

X-3

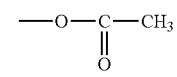

X-4

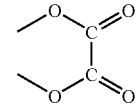

X-5

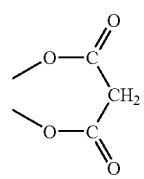

X-6

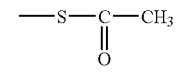

X-7

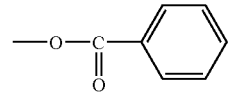

X-8

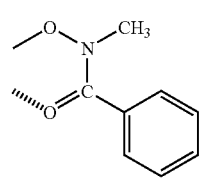

X-9

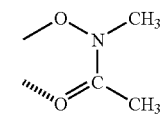

X-10

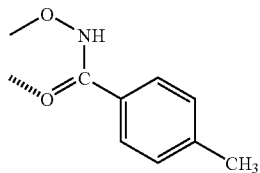

X-11

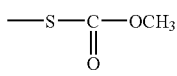

X-12

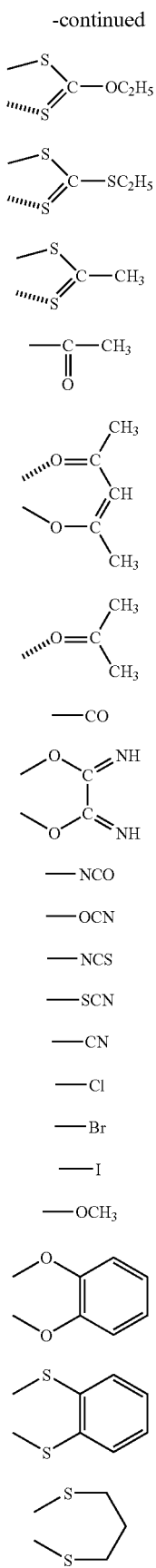
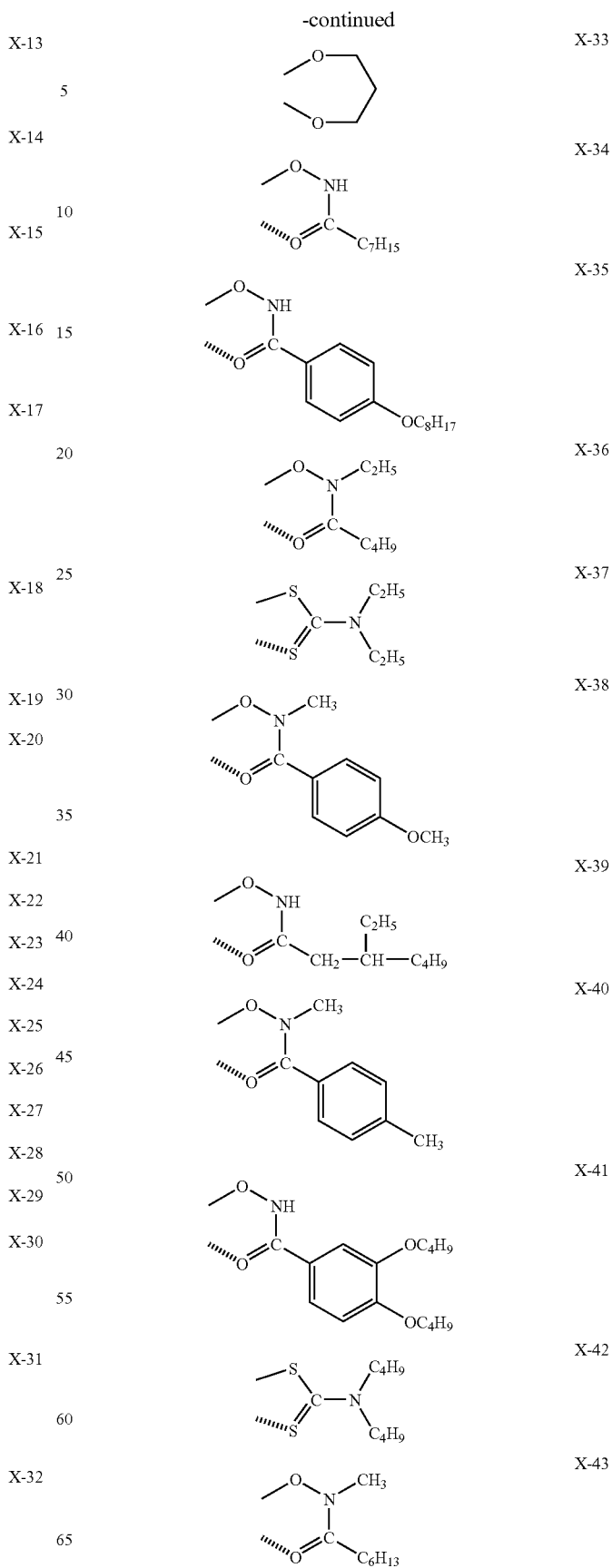

-continued
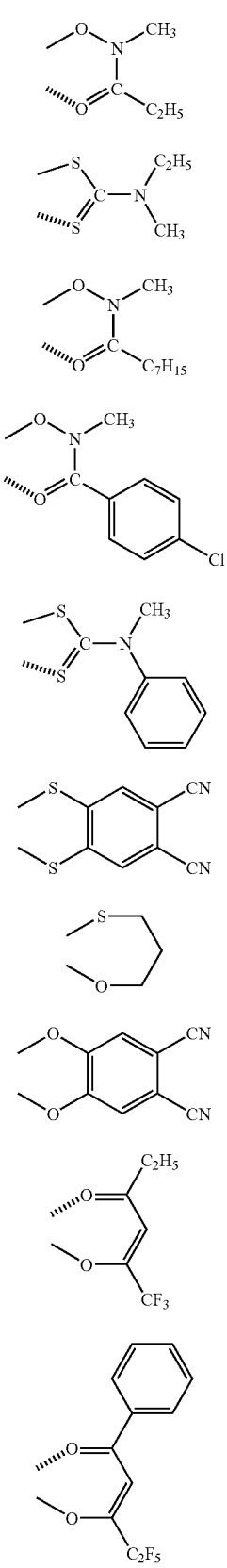
X-44
X-45
X-46
X-47
X-48
X-49
X-50
X-51
X-52
X-53
-continued
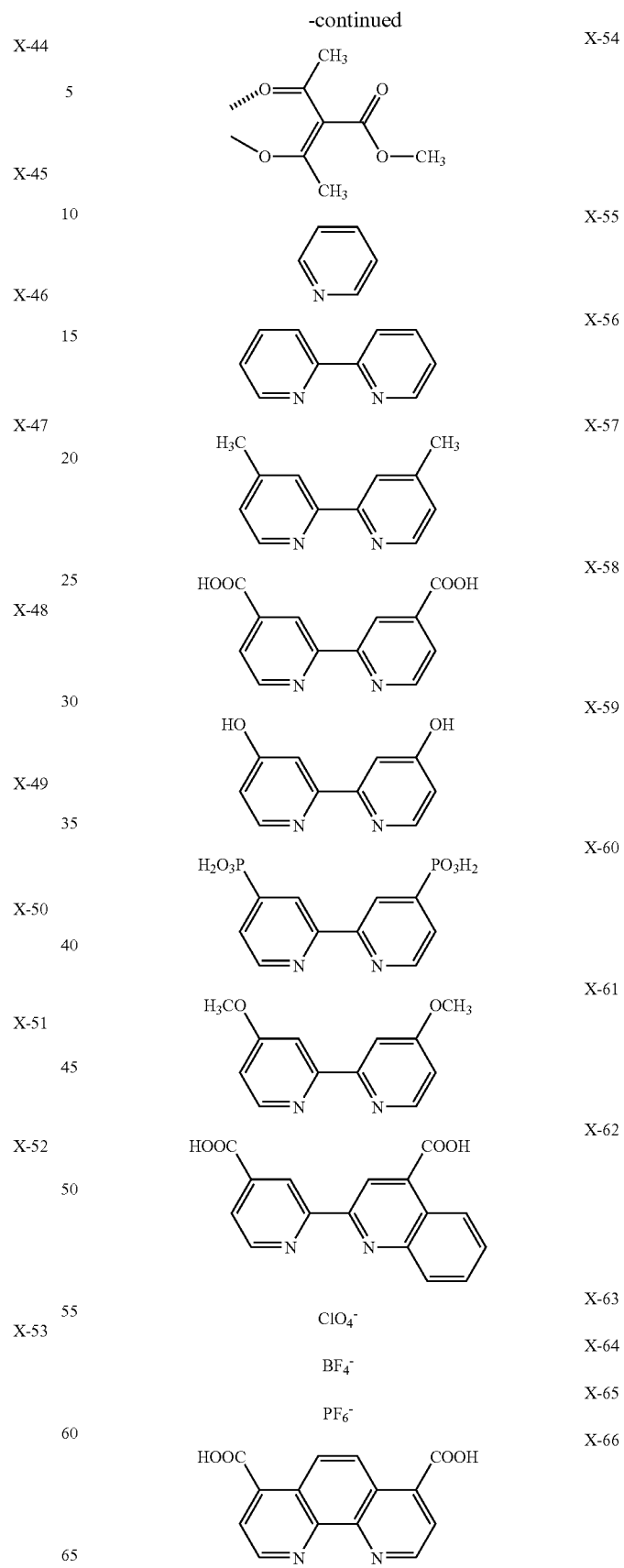
X-54
X-55
X-56
X-57
X-58
X-59
X-60
X-61
X-62
X-63
X-64
X-65
X-66

The metal complex dye which contains the dye ligand represented by the foregoing formula (1), preferably further contains a ligand represented by the following formula (2):

Formula (2)

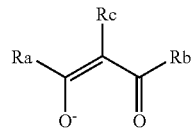

wherein Rc represents an alkyl group, an aryl group, an alkoxy group, an acyl group, an alkoxycarbonyl group, an aryloxycarbonyl group, a carbamoyl group, a halogen atom or a hydrogen atom; Ra and Rb each represent an alkyl group or an aryl group, which may be the same or different and Ra and Rc, or Rb and Rc may combine with each other to form a ring, provided that when Rc is a hydrogen atom, Ra and Rb are not methyl groups at the same time.

In the compound of formula (2), Rc is an alkyl group, an aryl group, an alkoxy group, an acyl group, an alkoxycarbonyl group, an aryloxycarbonyl group, a carbamoyl group, a halogen atom or a hydrogen atom. An electron-withdrawing group such as an aryloxy group, alkoxycarbonyl group or a halogen atom of Rc preferably stabilizes a metal ion-providing compound. Specifically, an aryloxy group or alkoxycarbonyl group is more preferred in terms of solubility. Examples of an aryloxy group include a phenoxycarbonyl group, and the alkoxycarbonyl group is, for example, one containing a straight or branched alkoxy group having 1 to 20 carbon atoms, such methoxycarbonyl, ethoxycarbonyl, pentylcarbonyl and 2-ethylhexyloxycarbonyl and the alkoxycarbonyl group may be substituted by a halogen atom, an aryl group or an alkoxy group.

Ra and Rb are each an alkyl group or an aryl group and may be the same with or different from each other; Ra and Rc, or Rb and Rc may combine with each other to form a ring, and when Rc is a hydrogen atom, Ra and Rb are not methyl groups at the same time. Examples of the alkyl group of Rc, Ra or Rb include a straight chain or branched alkyl group having 1 to 20 carbon atoms, such as methyl, ethyl, propyl, isopropyl, butyl, sec-butyl, tert-butyl, hexyl, octyl, and 2-ethylhexyl. Such an alkyl group may be substituted by a substituent such as a halogen atom, an aryl group, an alkoxy group. Examples of the aryl group of Rc, Ra or Rb include a phenyl or a naphthyl group, which may be substituted. The alkoxy group of Rc is, for example, a straight chain or branched alkoxy group having 1 to 20 carbon atoms, such as methoxy, ethoxy or butoxy. The acyl group of Rc is, for example, acetyl, propionyl, chloroacetyl, phenacetyl, and benzoyl. The halogenatom of Rc is preferably a chlorine atom.

Specific examples of a ligand represented by the foregoing formula (2) are shown below but are not limited to these.

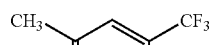
L-1

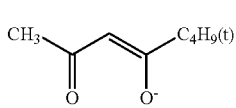
L-2

-continued

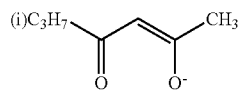
L-3

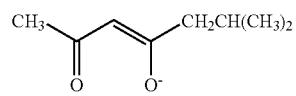
L-4

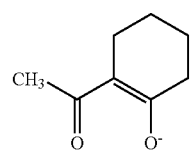
L-5

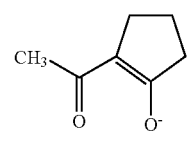
L-6

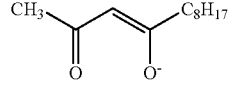
L-7

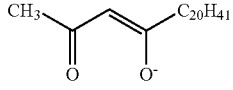
L-8

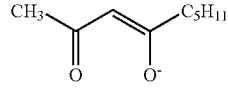
L-9

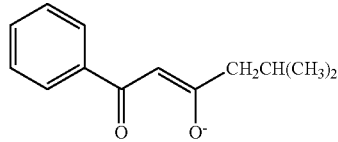
L-10

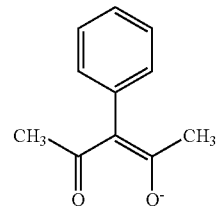
L-11

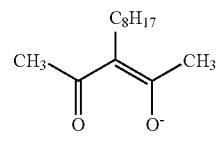
L-12

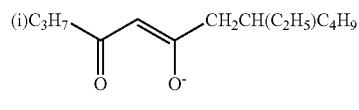
L-13

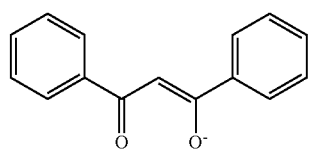
L-14

-continued
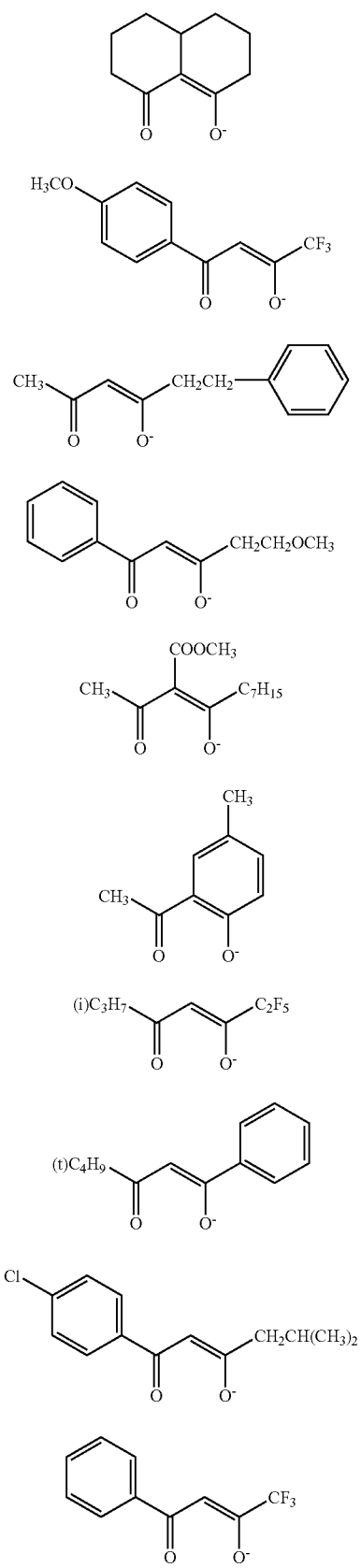
L-15
L-16
L-17
L-18
L-19
L-20
L-21
L-22
L-23
L-24
-continued
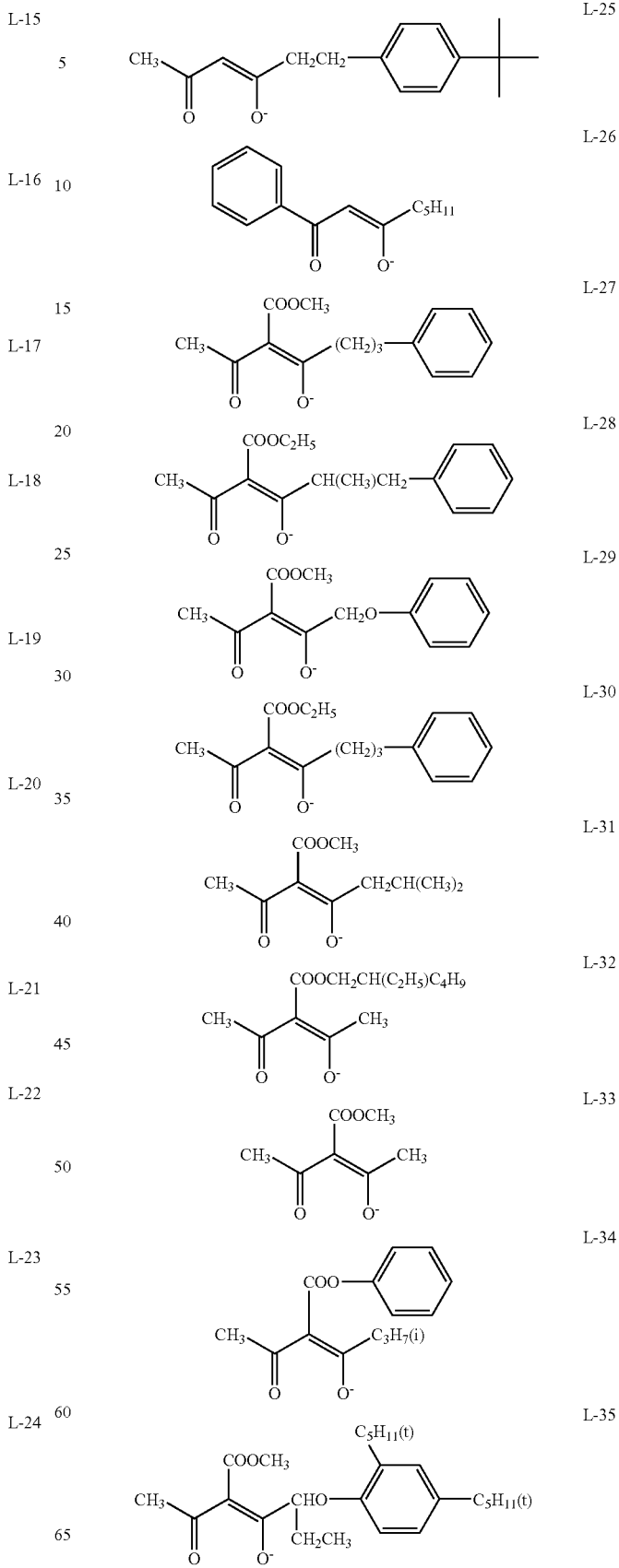
L-25
L-26
L-27
L-28
L-29
L-30
L-31
L-32
L-33
L-34
L-35

-continued

-continued

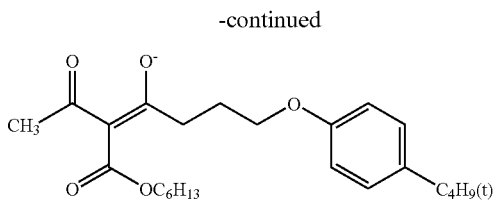
L-54

Specific examples of a metal complex dye containing a ligand of the foregoing formula (1) are shown below.

TABLE 1

| Compound No. | Metal Ion | Ligand of Formula (1) | Ligand or Counter Salt | | |
|---|---|---|---|---|---|
| MD-1 | $Ni^{2+}$ | 1 | 1 | X-26 | X-26 | — |
| MD-2 | $Ni^{2+}$ | 7 | 7 | X-26 | X-26 | — |
| MD-3 | $Ni^{2+}$ | 13 | 13 | X-26 | X-26 | — |
| MD-4 | $Ni^{2+}$ | 15 | 15 | X-64 | X-64 | — |
| MD-5 | $Ni^{2+}$ | 16 | 16 | X-4 | X-4 | — |
| MD-6 | $Ni^{2+}$ | 18 | 18 | X-23 | X-23 | — |
| MD-7 | $Ni^{2+}$ | 24 | 24 | X-26 | X-26 | — |
| MD-8 | $Ni^{2+}$ | 32 | 32 | X-26 | X-26 | — |
| MD-9 | $Ni^{2+}$ | 36 | 36 | X-4 | X-4 | — |
| MD-10 | $Ni^{2+}$ | 39 | 39 | X-64 | X-64 | — |
| MD-11 | $Ni^{2+}$ | 42 | 42 | X-65 | X-65 | — |
| MD-12 | $Ni^{2+}$ | 47 | 47 | X-26 | X-26 | — |
| MD-13 | $Ni^{2+}$ | 52 | 52 | X-4 | X-4 | — |
| MD-14 | $Ni^{2+}$ | 55 | 55 | X-26 | X-26 | — |
| MD-15 | $Ni^{2+}$ | 64 | 64 | X-64 | X-64 | — |
| MD-16 | $Ni^{2+}$ | 69 | 69 | X-63 | X-63 | — |
| MD-17 | $Ni^{2+}$ | 76 | 76 | X-4 | X-4 | — |
| MD-18 | $Ni^{2+}$ | 80 | 80 | X-26 | X-26 | — |
| MD-19 | $Ni^{2+}$ | 85 | 85 | X-26 | X-26 | — |
| MD-20 | $Ni^{2+}$ | 94 | 94 | X-4 | X-4 | — |
| MD-21 | $Ni^{2+}$ | 97 | 97 | X-26 | X-26 | — |
| MD-22 | $Ni^{2+}$ | 100 | 100 | X-26 | X-26 | — |
| MD-23 | $Ni^{2+}$ | 106 | 106 | X-64 | X-64 | — |
| MD-24 | $Ni^{2+}$ | 110 | 110 | X-23 | X-23 | — |
| MD-25 | $Ni^{2+}$ | 112 | 112 | X-65 | X-65 | — |
| MD-26 | $Ni^{2+}$ | 127 | 127 | X-26 | X-26 | — |
| MD-27 | $Ni^{2+}$ | 130 | 130 | X-64 | X-64 | — |
| MD-28 | $Ni^{2+}$ | 135 | 135 | X-65 | X-65 | — |
| MD-29 | $Ni^{2+}$ | 145 | 145 | X-26 | X-26 | — |
| MD-30 | $Ni^{2+}$ | 148 | 148 | X-4 | X-4 | — |
| MD-31 | $Ni^{2+}$ | 1 | 1 | X-54 | X-54 | — |
| MD-32 | $Ni^{2+}$ | 7 | 7 | L-19 | L-19 | — |
| MD-33 | $Ni^{2+}$ | 13 | 13 | L-19 | L-19 | — |
| MD-34 | $Ni^{2+}$ | 15 | 15 | X-52 | X-52 | — |
| MD-35 | $Ni^{2+}$ | 16 | 16 | X-53 | X-53 | — |
| MD-36 | $Ni^{2+}$ | 18 | 18 | L-19 | L-19 | — |
| MD-37 | $Ni^{2+}$ | 24 | 24 | L-51 | L-51 | — |
| MD-38 | $Ni^{2+}$ | 32 | 32 | L-52 | L-52 | — |
| MD-39 | $Ni^{2+}$ | 36 | 36 | L-19 | L-19 | — |
| MD-40 | $Ni^{2+}$ | 39 | 39 | L-19 | L-19 | — |
| MD-41 | $Ni^{2+}$ | 42 | 42 | L-12 | L-12 | — |
| MD-42 | $Ni^{2+}$ | 47 | 47 | X-53 | X-53 | — |
| MD-43 | $Ni^{2+}$ | 52 | 52 | L-19 | L-19 | — |
| MD-44 | $Ni^{2+}$ | 55 | 55 | L-19 | L-19 | — |
| MD-45 | $Ni^{2+}$ | 64 | 64 | L-52 | L-52 | — |
| MD-46 | $Ni^{2+}$ | 69 | 69 | L-35 | L-35 | — |
| MD-47 | $Ni^{2+}$ | 76 | 76 | L-47 | L-47 | — |
| MD-48 | $Ni^{2+}$ | 80 | 80 | L-27 | L-27 | — |
| MD-49 | $Ni^{2+}$ | 85 | 85 | L-19 | L-19 | — |
| MD-50 | $Ni^{2+}$ | 94 | 94 | X-53 | X-53 | — |
| MD-51 | $Ni^{2+}$ | 97 | 97 | L-19 | L-19 | — |
| MD-52 | $Ni^{2+}$ | 100 | 100 | L-19 | L-19 | — |
| MD-53 | $Ni^{2+}$ | 106 | 106 | L-54 | L-54 | — |
| MD-54 | $Ni^{2+}$ | 110 | 110 | L-52 | L-52 | — |
| MD-55 | $Ni^{2+}$ | 112 | 112 | L-21 | L-21 | — |
| MD-56 | $Ni^{2+}$ | 127 | 127 | L-19 | L-19 | — |
| MD-57 | $Ni^{2+}$ | 130 | 130 | X-53 | X-53 | — |
| MD-58 | $Ni^{2+}$ | 135 | 135 | L-39 | L-39 | — |
| MD-59 | $Ni^{2+}$ | 145 | 148 | L-19 | L-19 | — |
| MD-60 | $Ni^{2+}$ | 145 | 148 | X-53 | X-53 | — |
| MD-61 | $Zn^{2+}$ | 13 | 13 | X-26 | X-26 | — |

TABLE 1-continued

| Compound No. | Metal Ion | Ligand of Formula (1) | Ligand or Counter Salt | | |
|---|---|---|---|---|---|
| MD-62 | $Zn^{2+}$ | 22 | 22 | X-26 | X-26 | — |
| MD-63 | $Zn^{2+}$ | 53 | 53 | X-65 | X-65 | — |
| MD-64 | $Zn^{2+}$ | 80 | 80 | X-26 | X-26 | — |
| MD-65 | $Zn^{2+}$ | 117 | 117 | X-26 | X-26 | — |
| MD-66 | $Zn^{2+}$ | 152 | 152 | L-19 | L-19 | — |
| MD-67 | $Zn^{2+}$ | 72 | 72 | L-52 | L-52 | — |
| MD-68 | $Zn^{2+}$ | 110 | 110 | L-54 | L-54 | — |
| MD-69 | $Zn^{2+}$ | 133 | 133 | L-19 | L-19 | — |
| MD-70 | $Cu^{2+}$ | 13 | 13 | X-26 | X-26 | — |
| MD-71 | $Cu^{2+}$ | 53 | 53 | X-26 | X-26 | — |
| MD-72 | $Cu^{2+}$ | 113 | 113 | X-64 | X-64 | — |
| MD-73 | $Cu^{2+}$ | 139 | 139 | X-4 | X-4 | — |
| MD-74 | $Cu^{2+}$ | 143 | 143 | L-19 | L-19 | — |
| MD-75 | $Cu^{2+}$ | 76 | 76 | L-53 | L-53 | — |
| MD-76 | $Cu^{2+}$ | 99 | 99 | L-37 | L-37 | — |
| MD-77 | $Cu^{2+}$ | 141 | 141 | L-30 | L-30 | — |
| MD-78 | $Co^{2+}$ | 13 | 13 | X-26 | X-26 | — |
| MD-79 | $Co^{2+}$ | 54 | 54 | L-19 | L-19 | — |
| MD-80 | $Fe^{2+}$ | 52 | 52 | X-26 | X-26 | — |
| MD-81 | $Fe^{2+}$ | 134 | 134 | L-19 | L-19 | — |
| MD-82 | $Ru^{2+}$ | 13 | 13 | X-23 | X-23 | — |
| MD-83 | $Ru^{3+}$ | 109 | 109 | X-26 | X-26 | X-26 |
| MD-84 | $Ti^{3+}$ | 51 | 51 | X-26 | X-26 | X-26 |
| MD-85 | $Ti^{3+}$ | 144 | 144 | L-19 | L-19 | X-26 |

In the following, the manufacturing method to obtain a toner of the invention will be described. The conventionally employed manufacturing method of toners is a so-called pulverization method, in which resin and a colorant, and optionally a mold-releasing agent or a charge-controlling agent are mixed in the form of a powder, and subsequently, sufficiently heated melt the resin and application of a shearing force thereto allows the additives to be dispersed in the resin (melt-kneading), thereafter, the melted mixture is cooled, pulverized and dispersed to obtain a toner having the intended particle size and particle size distribution. The form of toner particles obtained by the pulverization method is irregular.

On the other hand, a polymerization method comprises forming individual polymer particles from a monomer and allowing a colorant or the like to be included within the polymer particles to obtain toner particles. Suspension polymerization and emulsion polymerization aggregation are typical methods of the above.

Manufacturing methods to obtain toners of the invention are not specifically limited but a method of manufacturing toner by the polymerization method is preferably employed. Thus, to stabilize the particle form, manufacturing a toner by the polymerization method forms toner particles of a uniform shape to a certain level and the particles are dried in the fluidized state to obtain more rounded particles.

Either a suspension polymerization method or an emulsion aggregation method is applicable in the invention. In the former method, toner constituents such as a colorant and a releasing agent are dispersed in a polymerizable monomer and suspended in water and the suspended particles are polymerized to obtain toner particles. In the latter method, resin particles are prepared through emulsion polymerization and the obtained resin particles are mixed with a dispersion of toner constituents such as a colorant to be aggregated with each other to obtain toner particles. In general, the emulsion aggregation method is more suitable. In the suspension polymerization method, the particles become irregular shapes, which necessitates a subsequent pulverization process, producing problems such that roundness of the shape is vitiated by the concurrent impact force.

In the invention, particles prepared by the polymerization method are dried in heated airflow to achieve the further enhanced constitution of the invention. The reason therefor is not definite but it is assumed that the heating dry is performed in the airflow in the presence of excessive moisture in the extremely minute region, and the portion swelled with moisture is heated to cause a change in shape, resulting in slightly rounded particle forms. It is preferred to perform this airflow heating treatment in the falling-rate drying stage.

In this regard, it is preferred that at least 10 wt % of water per polymer particles exists therein. Thus, when heated in the airflow, the particles becoming a high temperature often cause problems such that the shape becomes spherical or the surface composition changes. To prevent the particle from being heated to a temperature causing softening of the particles, it is preferred to have a moisture content of at least 10% by weight. This method does not raise the temperature of the particles to the point of softening and the overall shape of the toner particles becoming spherical is not promoted. The upper limit of the moisture content is not specifically limited but it is usually 50%. The presence of water in an amount exceeding this results in deficiency in thermal transfer and renders it difficult to achieve a uniform shape.

Examples of an airflow drying apparatus include a so-called spray drying apparatus, a vibration fluidized-bed drying machine, a high-speed fluidized drying machine and flash jet drier, in which the suitable airflow temperature is from 30 to 200° C.

A color toner (hereinafter, also denoted simply as a toner) of the invention contains at least a resin and a colorant, and a releasing agent or a charge controlling agent as an improver for fixation may optionally be contained. Contrary to the foregoing toner particles mainly composed of a resin and a colorant, those which are added with an external additive comprised of inorganic particles or organic particles, are also usable. In this case, one which incorporates an external additive is called a toner, while one which is prior to incorporation of the external additive is called colored particles.

The toner of the invention is prepared preferably by the process of allowing resin particles to be aggregated in an aqueous medium. For example, an emulsion of needed additives is added to a solution and further thereto, a monomer is added to prepare polymer microparticles and thereafter, an organic solvent or a coagulant is added thereto to cause aggregation. Examples of such a preparation method include a method in which a dispersion of a releasing agent or a colorant as a constituent of a toner is mixed with polymer particles in the aggregation stage and a method in which a releasing agent or a colorant is dispersed in a monomer to perform emulsion polymerization. Herein, the aggregation indicates plural resin particles being fused.

Preparation of the above can be performed through suspension polymerization, in which to make the shape indeterminate, polymer particles are subjected to a mechanical impact force to form particles of an indeterminate form and thereafter, it is necessary to control the shape.

Methods of preparing the toner of the invention are not limited to those described above, but it is prepared preferably in such a manner that particles are formed according to the methods described in JP-A Nos. 5-265252, 6-329947 and 9-15904 and then subjected to a heat treatment. Thus, the toner of the invention can be formed by a method of allowing fine particles composed of resin, a colorant and the like to be aggregated, specifically in such a manner that these particles are dispersed in water using a surfactant, a coagulant is added thereto at a concentration higher than the critical coagulation concentration to cause salting out, the aggregated particles are fused with heating at a temperature higher than the glass transition temperature of the resin, and the thus obtained particles containing water are dried with heating in the fluidized state. In this case, an organic solvent which is infinitely soluble in water, may be added simultaneously with the coagulant.

Specific examples of a monomer constituting the resin used in the invention include styrene or styrene derivatives such as styrene, o-styrene, m-styrene, p-methylstyrene, α-methylstyrene, p-chlorostyrene, 3,4-dichlorotyrene, p-phenylstyrene, p-ethylstyrene, 2,4-dimethylstyrene, p-t-butylstyrene, p-n-hexylstyrene, p-n-octylstyrene, p-n-nonylstyrene, p-n-decylstyrene, and p-n-dodecylstyrene; methacrylic acid ester derivatives such as methyl methacrylate, ethyl methacrylate, n-butyl methacrylate, isopropyl methacrylate, isobutyl methacrylate, t-butyl methacrylate, n-octyl methacrylate, 2-ethylhexyl methacrylate, stearyl methacrylate, lauryl methacrylate, phenyl methacrylate, diethylaminoethyl methacrylate, and dimethylaminoethyl methacrylate; acrylic acid ester derivatives such as methyl acrylate, ethyl acrylate, isopropyl acrylate, n-butylacrylate, t-butyl acrylate, isobutyl acrylate, n-octyl acrylate, 2-ethylhexyl acrylate, stearyl acrylate, lauryl acrylate, and phenyl acrylate; olefins such as ethylene propylene and isobutylene; halogenated vinyls such as vinyl chloride, vinylidene chloride, vinyl bromide, vinyl fluoride, vinylidene fluoride; vinyl ethers such as vinyl propionate, vinyl acetate, vinyl benzoate; vinyl ethers such as vinyl methyl ether and vinyl ethyl ether; vinyl ketones such as vinyl methyl ketone, vinyl ethyl ketone and vinyl hexyl ketone; N-vinyl compounds such as N-vinylcarbazole, N-vinylindole, and N-vinylpyrrolidone; vinyl compounds such as vinylnaphthalene and vinylpyridine; and acrylic acid or methacrylic acid derivatives such as acrylonitrile, methacrylonitrile and acrylamide. These vinyl type monomers can be used singly or in combination.

Monomers containing an ionically dissociative group may be used in combination with the foregoing monomers. Such monomers contain a substituent group such as a carboxyl group, sulfonic acid group, and phosphoric acid group and specific example thereof include acrylic acid, methacrylic acid, maleic acid, itaconic acid, cinnamic acid, fumaric acid, maleic acid monoalkyl esteritaconic acid monoalkyl ester, styrenesulfonic acid, allylsulfonic acid, 2-acrylamido-2-methylpropanesulfonic acid, acidphosphooxyethyl methacrylate, and 3-chloro2-acidphosphooxypropyl methacrylate.

Resin having a crosslinked structure can be formed using polyfunctional vinyls, such as divinylbenzene, ethylene glycol dimethacrylate, ethylene glycol diacrylate, diethylene glycol dimethacrylate, diethylene glycol diacrylate, triethylene glycol dimethacrylate, triethylene glycol diacrylate, neo-pentylglycol dimethacrylate, and neo-pentylglycol diacrylate.

These monomers can be polymerized using a radical polymerization initiator. In suspension polymerization, oil-soluble polymerization initiators are usable. Examples of anoil-soluble polymerization initiator include azoisobutylonitrile, lauryl peroxide, and benzoyl peroxide. Water-soluble radical polymerization initiators are usable when employing emulsion polymerization. Examples of a water-soluble radical polymerization initiator include persulfates such as potassium persulfate and ammonium persulfate, azo-bisaminodipropane acetate, azobiscyanovaleric acid and its salt, and hydrogen peroxide.

Of resins used in the invention, those which exhibit a glass transition point of 20 to 90° C. or those which exhibit a softening point of 80 to 220° C. are preferred. The glass transition point can be determined by the differential thermal analysis, and the softening point can be determined using a Kohka-type flow tester. These resins preferably have a number-average molecular weight (Mn) of 1000 tp 100000 and a weight-average molecular weight (Mw) of 2000 to 1000000, which are determined by the gel permeation chromatography. The molecular weight distribution of Mw/Mn is preferably from 1.8 to 70.

Coagulants are not specifically limited but suitably chosen from metal salts. Specifically, there are cited salts of alkali metals such as sodium, potassium and lithium as a univalent metal, salts of alkaline metals such as calcium and magnesium as a bivalent metal, salts of bivalent metals such as manganese and copper, and salts of trivalent metals such as iron and aluminum.

These coagulants are added preferably in an amount of more than the critical coagulation concentration. The critical coagulation concentration is a measure with respect to stability of an aqueous dispersion, indicating a concentration at which coagulation occurs with addition of the coagulant. The critical coagulation concentration is variable depending on constituents to be emulsified and the dispersing agent, as described, for example, in S. Okamura et al, Kobunshi Kagaku 17, 601 (1960), Kobunshi-Gakkai, in which detailed critical coagulation concentrations can be determined. Alternatively, while adding an intended salt to the objective particle dispersion, the $\zeta$-potential of the dispersion is measured and a salt concentration at which the potential value varies, can be determined as a critical coagulation concentration.

A coagulant may be added at any amount more than the critical coagulation concentration but preferably at least 1.2 times the critical coagulation concentration, and more preferably at least 1.5 times.

The infinite-soluble solvent refers to a solvent which is infinitely soluble in water and solvents which do not dissolve the formed resin are chosen in the invention. Specific examples thereof include alcohols such as methanol, ethanol, propanol, isopropanol, t-butanol, methoxyethanol and butoxyethanol; nitrites such as acetonitrile, and ethers such as dioxane. Of these, ethanol, propanol and isopropyl alcohol are preferred. An infinite-soluble solvent is added preferably in an amount of 1% to 30.0% by volume of the polymer-containing dispersion after having been added with a coagulant.

After filtering the prepared colored particles, a slurry containing at least 10 wt % water per particles is preferably subjected to fluidized-bed drying to enhance uniformity of particle shape. In that case, a polymer containing a polar group is preferred. It is assumed that water more or less swells polymers containing a polar group, whereby uniformity of particle shape is easily achieved.

Besides metal complex dyes, carbon black, magnetic substances, dyes and pigments can optionally employed as a colorant for the toners of the invention. Carbon black such as channel black, furnace black, acetylene black and thermal black•lamp black are usable. As a magnetic substance are usable ferromagnetic metals such as iron, nickel and cobalt and alloys thereof; ferromagnetic metal compounds such as ferrite and magnetite; alloys which contain no ferromagnetic metal but are capable of exhibiting ferromagnetism upon thermal treatment, such as so-called Heusler's alloys, e.g., manganese-copper-aluminum and manganese-copper-tin; and chromium dioxide.

The metal complex dye may be used alone or in combination with other dyes. Examples of such dyes include C.I. Solvent Red 1, the said 49, the said 52, the said 58, the said 63, the said 111 and the said 122; C.I. Solvent Yellow 19, the said 44, the said 77, the said 79, the said 81, the said 82, the said 93, the said 98, the said 103, the said 104, the said 112, and the said 162; C.I. Solvent Blue 25, the said 36, the said 60, the said 70, the said 93 and the said 95. A mixture thereof is also usable. Examples of pigments include Pigment Red 5, the said 48:1, the said 53:1, the said 57:1, the said 122, the said 139, the said 144, the said 149, the said 166, the said 177, the said 178, the said 222; C.I. Pigment Orange 31 and the said 43; C.I. Pigment Green 7; C.I. Pigment Blue 15:3 and the said 60; and their mixtures. The number-average primary particle size, depending on the kind thereof, is preferably from 10 to 200 nm.

Colorants can be added in the following manner. At the stage when polymer particles prepared by emulsion polymerization aggregate following addition of a coagulant, a pigment is added to color the polymer. Alternatively, in the stage of polymerizing monomers, a colorant is added and polymerization is performed to obtain colored particles. In cases when adding a colorant during the course of polymerization, it is preferred to subject the colorant to a surface treatment using a coupling agent or the like, but which may not inhibit radical polymerization capability.

The metal complex dye of the invention can be obtained by forming a complex, followed by addition of a dye, or by separately adding a metal ion-donating material (e.g., nickel chloride) and a ligand of formula (1) to form a complex therein.

There may be added low molecular weight polypropylene (number-average molecular weight of 1500 to 9000) or low molecular weight polyethylene to improve fixing capability. Azo type metal complexes or quaternary ammonium salts may be incorporated as a charge controlling agent. In order to provide fluidity, polymer particles of inorganic or organic microparticles may be externally added to toner particles (colored particles). In that case, inorganic microparticles of silica, titania or alumina are preferred. It is also preferred to treat the inorganic microparticles with a silane coupling agent or a titanium coupling agent to enhance hydrophobicity.

The volume-average toner particle size is preferably 3 to 9 μm in the invention. The particle size can be controlled by a coagulant concentration, an addition amount of an organic solvent and the polymer composition. The volume-average toner particle size can be determined using Coulter Counter TA-II or Coulter Multisizer.

The toner of the invention can be used in any of the cases using a single-component toner containing a magnetic substance, using a two-component developer together with a carrier, and using a non-magnetic toner alone. Of these, using a two-component developer together with a carrier is preferred. There can be used a non-coated carrier composed of only a magnetic material such as ferrite or a resin-coated carrier in which the magnetic material particle surface is coated with resin. The volume-average size of carrier particles is preferably from 30 to 150 μm. Coating resin is not specifically limited but, for example, styrene-acryl resin or silicone resin is preferred.

Image Forming Method

Development systems capable of using the toners of the invention are not specifically limited and are suitably applicable to a contact development system or a non-contact development system. The toner of the invention, which exhibits a high charge-rising characteristic, is advantageous in a non-contact development system. In the non-contact development system in which the developing field greatly varies, a minute variation of charge greatly affects development itself. The toner of the invention, which exhibits a high charge-rising characteristic, results in less variation in charge and thereby sufficient electrostatic charge can be stably gained so that images can stably be formed over a long term even in the non-contact development system.

In this contact development system, the layer thickness of a developer containing the toner of the invention is usually from 0.1 to 8 mm in the development region, and preferably from 0.4 to 5 mm. The gap between a photoreceptor and a developer carrying member is usually from 0.15 to 7 mm and preferably from 0.2 to 4 mm.

In the non-contact development system, in which a developer layer formed on a developer carrying member is not in contact with a photoreceptor, the developer layer is formed preferably as a thin, layer to constitute this development system. This system forms a 20 to 500 μm thick developer layer in the development region on the developer carrying member surface, and a gap between the photoreceptor and the developer carrying member being more than the thickness of the developer layer. The foregoing thin layer formation is performed by means of a magnetic blade employing magnetic force or by a system of compressing a developer layer-controlling bar onto the developer carrying member surface. There is also feasible a method in which a urethane blade or a phosphor bronze plate is brought into contact with the developer carrying member surface to control the developer layer. The compression force of a compression-controlling member is suitably from 1 to 15 gf/mm. A lesser compression force is insufficient in controlling force, leading to unstable conveyance. On the other hand, an excessively large compressing force increases stress to the developer, resulting in lowering in durability of the developer. The preferred range is from 3 to 10 gf/mm. The gap between the developer carrying member and the photoreceptor surface needs to be greater than the developer layer thickness. When applying development bias, either only a direct current component may be provided or an alternating current bias may be applied.

The diameter of a developer carrying member is preferably from 10 to 40 mm. A lesser diameter results in insufficient mixing of the developer, rendering it difficult to achieve sufficient mixing to charge the toner. An excessively larger diameter magnifies the centrifugal force to the developer, tendering to cause problems such as scattering of the toner.

Hereinafter, an example of a non-contact development system is described using FIG. 1. FIG. 1 illustrates the developing section of a non-contact development system in which the image forming method of the invention can suitable be conducted; the numerals 1 and 2 designate a photoreceptor and a developer carrying member, 3 is a two-component developer containing the toner of the invention, 4 is a developer layer-controlling member, 5 is a development region, 6 is a developer layer and 7 is a power source necessary to form an alternating field.

The two-component developer containing the toner of the invention is held by a magnetic force on the developer carrying member 2 internally having a magnet 2B and movement of a development sleeve 2A conveys the developer to the development region 5. During conveyance, the thickness of the developer layer 6 is controlled by the developer layer-controlling member so that the developer layer is not brought into contact with the photoreceptor. The minimum gap (Dsd) in the development region is more than the thickness of the developer layer 6 (preferably 20 to 500 μm) and extents of 100 to 1000 μm. The power source 7 to form an alternating field preferably supplied an alternating current having an frequency of 1 to 10 kHz and a voltage of 1 to kVp-p. A direct current is preferably 300 to 800 V.

Figure 2:
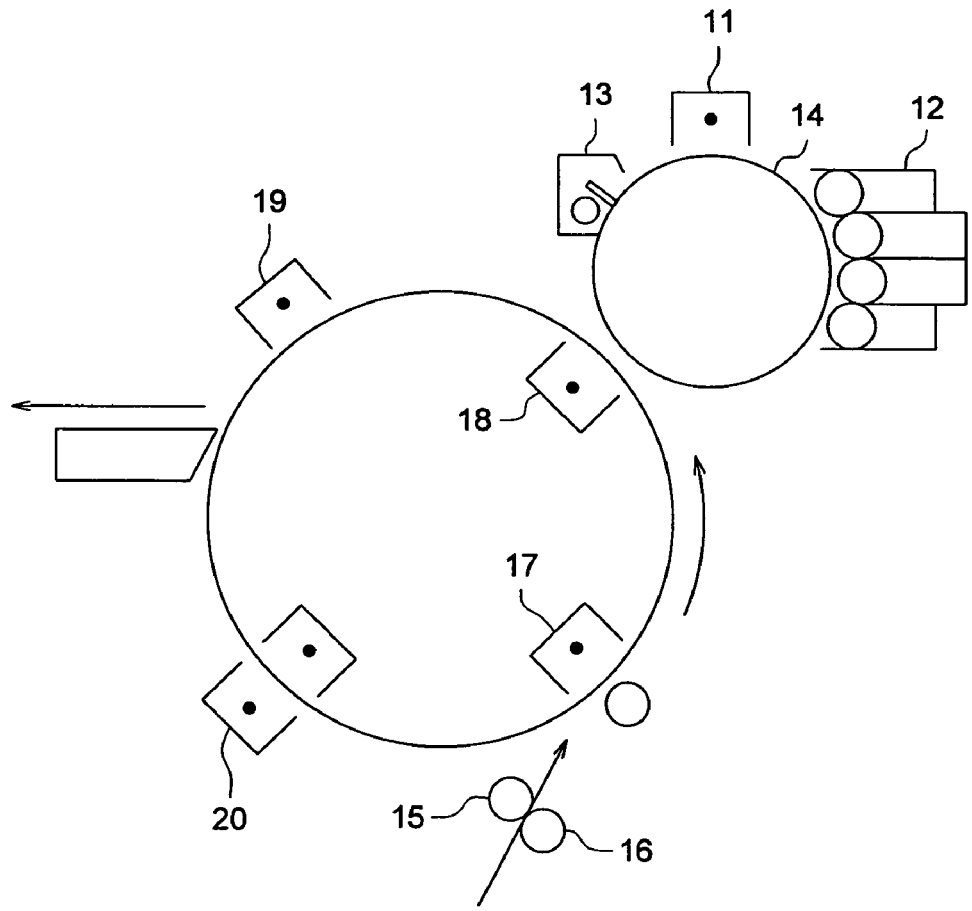
FIG. 2 illustrates an example of a sequential transfer system.
Figure 3:
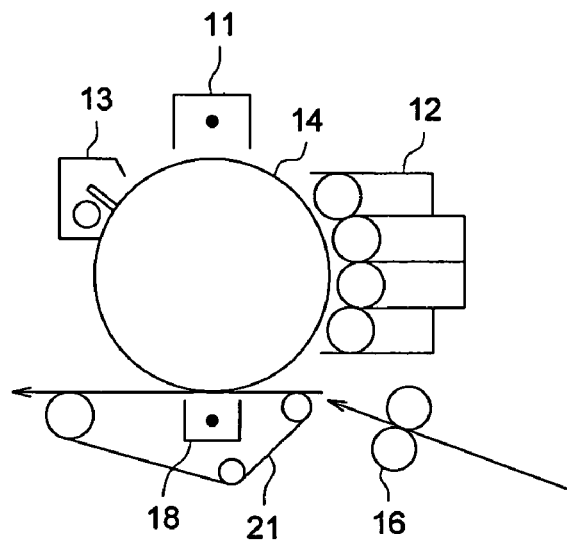
FIG. 3 illustrates an example of a batch transfer system.

Application of the toner of the invention to a color image forming system includes, for example, a system in which monochromatic images are formed on the photoreceptor and transferred onto the image support sequentially (which is denoted as a sequential transfer system, as shown in FIG. 2) or a system in which plural monochromatic images are developed on the photoreceptor to form a color image and transferred in a lump to the image support (which is denoted as a batch transfer system, as shown in FIG. 3). The specification describes that a latent image is formed and subjected to toner development on a photoreceptor, but it is not limited specifically only to the photoreceptor but may be any static latent image support having the foregoing functions.

The image forming system in FIGS. 2 and 3 will be further described below. As shown in FIG. 1, 1 or 3, a developing machine including the magnet 2B in its interior is used as a developer carrying member and the sleeve 2A forming the surface of the developer carrying member employs aluminum, surface-treated aluminum or stainless steel.

An example of a sequential transfer system is described in FIG. 2. The numeral 11 is a charger as a charging electrode and 12 is a development unit comprising developing machine loaded with the respective yellow, magenta, cyan and black toners, which are divided into four vessels corresponding to the four toners. The basic constitution of the developing machine is the same as the illustration of the developing section shown in FIG. 1. The numeral 14 is a photoreceptor drum, 13 is a cleaning unit, 15 is transfer drum in which a monochromatic toner image formed on the photoreceptor drum is temporarily held, further thereon, the subsequent monochromatic toner image is held and finally, the desired multi-color image is formed, 16 is a conveyance unit to convey the transfer material onto which a toner image on the transfer drum is transferred, 17 is an adsorption electrode which is provided in the interior of transfer drum 15, corona-discharges from the interior and allows the transfer material to be electrostatically adsorbed on the drum, 18 is a transfer electrode which allows a toner image formed on the photoreceptor drum 14 to be sequentially transferred on the transfer drum, 19 is a release electrode which releases the transfer material electrostatically adsorbed onto the transfer drum 15, and 20 is a removing electrode to remove any residual charge remaining on the transfer drum.

The photoreceptor drum 14 is uniformly charged thereon by the charger 11 and thereafter, imagewise exposure (which is not shown in the figure) is conducted to form an electrostatic latent image. The electrostatic latent image is subsequently developed by a developing machine containing a toner of a single color (for example, black) of the development unit 12 to form a single color toner image on the photoreceptor drum 14. The transfer material which has been conveyed by the conveyance unit 16 to the transfer drum 15, is electrostatically adsorbed onto the transfer drum by the adsorption electrode 17 and conveyed to the transfer section.

In the transfer section, the foregoing toner image formed on the photoreceptor drum 14 is transferred onto the conveyed transfer material. On the photoreceptor drum 14 after having transferred the transfer image, any toner still remains and the remained toner is removed by the cleaning unit 13 and used in the subsequent process. In the case of multi-color image formation, following a similar process, toner images of other colors are formed through development and are sequentially transferred onto the transfer drum 15. Finally, the intended toner image is formed on the transfer material adsorbed onto the transfer drum 15. The transfer material after having formed the intended toner image is released by the release electrode 19 and conveyed to the fixation section to obtain a finally fixed multi-color toner image. On the other hand, the transfer drum 15 removes remaining charge by the removing electrode 20 and used in the subsequent process.

Next, a batch transfer system will be described based on FIG. 3. Descriptions of the respective sections of the apparatus, which are the same as shown in FIG. 2, are omitted, but the numeral 21 is a conveyance section to transfer the toner image, while conveying the conveyed transfer material. A charge is uniformly formed on the photoreceptor drum 14 using a charging electrode and then an electrostatic latent image is formed by a latent image forming means (which is not shown in the figure). The electrostatic latent image is developed by the developing machine having a toner of a single color (for example, black) of the developing unit 12 to form a single-color toner image on the photoreceptor drum. In the FIG., on the photoreceptor drum having the toner image without removing this image, a charge is uniformly formed by the charging electrode 11, further, an electrostatic latent image is formed and developed by a developing machine having a toner of a different color from the foregoing, and the thus formed toner image of another color is superposed onto the prior toner image to form an image. In the meanwhile, the cleaning unit 13, the transfer electrode 18 and the conveyance section 21 do not operate and turned out from the photoreceptor drum 14 so that the toner image on the photoreceptor drum 14 is not perturbed.

After completing the intended image formation and forming a multi-color image, the toner image on the photoreceptor drum is transferred onto a transfer material conveyed by the conveyance unit 16, while conveying to the conveyance section 21. The transfer material having the transferred toner image is conveyed to the fixation section and fixed to form a final multi-color toner image on the transfer material. On the photoreceptor drum 14 after having transferred the toner image, the toner still remains and the remained toner is removed by the cleaning unit 13 and used in the subsequent process.

The toner image which are formed on the photoreceptor by the various systems described above, is transferred onto a transfer material such as paper through the transfer process. The transfer system is not specifically limited and can employ a so-called corona transfer system or roller transfer system.

After having transferred the toner image, the toner still remains On the photoreceptor and the remained toner is cleaned by cleaning and used in the subsequent process.

In the invention, the cleaning mechanism is not specifically limited and conventionally known cleaning mechanisms are arbitrarily usable, such as a blade cleaning system, a magnetic brush cleaning system and a fur brush cleaning system. The preferred cleaning mechanism is a blade cleaning system employing a so-called cleaning blade.

The suitable fixation method of the invention is a heated roller fixation system. This system is formed of an upper roller of a metallic cylinder of iron or aluminum covered with tetrafluoroethylene or tetrafluoroethylene-perfluroalkoxyvinyl ether copolymer, including a heat source in its interior, and a lower roller of silicone rubber or the like. A linear heater is included as a heat source and the surface of the upper roller is typically heated to a temperature of 120 to 200° C. In the fixation section, pressure is applied between the upper roller and the lower roller to deform the lower roller, forming a so-called nip. The nip width is usually 1 to 10 mm, and preferably 1.5 to 7 mm. The fixing linear speed is preferably 40 to 400 mm/sec. An excessively narrow nip becomes difficult to uniformly provide heat to the toner, causing uneven fixation. On the other hand, a broad nip promotes fusion of resin, producing problems such as fixing off-set being excessive.

A fixation cleaning mechanism may be used, in which a system of supplying silicone oil to an upper fixing roller, a film supplying system or a method of cleaning with a pad, roller or web impregnated with silicone oil.

Color Filter

There are employed various dispersing means such as a two-roll mill, three-roll mill, a sand mill and a kneader to disperse the compound of the invention for use in a color filter.

Conventionally known varnishes used in colored compositions for color filters are employed as a resin varnish used to disperse compounds to form colored composition. Solvents or aqueous medium suitable for resin varnish are used as a disperse medium. Further, there may optionally used commonly known additives such as a dispersing aid, a lubricant or an adhesion-promoting agent.

Photosensitive resin varnish and non-photosensitive varnish are employed as resin varnish. Photosensitive resin varnish for use in an ultraviolet curing ink or an electron beam curing ink is cited. Examples of a non-photosensitive varnish include varnishes for use in printing ink, such as a letterpress ink, a lithographic printing ink, an intaglio gravure printing ink, and a screen printing ink; varnishes used for electropainting; varnishes used for a developer for electronic printing or electrostatic printing; and varnishes for use in thermal transfer ribbons.

Examples of a photosensitive resin varnish include varnishes of photosensitive cyclization rubber type resin, photosensitive phenol type resin, photosensitive polymethacrylate type resin, photosensitive polyamide type resin, or photosensitive polyimide type resin; and varnished of unsaturated polyester type resin, polyester acrylate type resin, polyepoxyacrylate type resin, polyurethane acrylate type resin, polyether acrylate type-resin or polyol acrylate resin. There is also cited a varnish containing monomers as a reactive diluent. To the compound of the invention and the foregoing varnish is added a photopolymerization initiator such as benzoin ether or benzophenone and kneaded to obtain a photosensitive coloring composition of the invention. Replacement of the above-described photopolymerization initiator by a thermal polymerization initiator can obtain a photosensitive coloring composition. Using the foregoing photosensitive coloring composition, formation of a pattern of a color filter can conducted, for example, in the following manner. Thus, the photosensitive coloring composition is coated overall on the transparent substrate using spin coat, a low speed rotary coater, a roll coater or a knife coater, or over-all printing or partial printing slightly larger than the pattern is conducted employing various printing methods. After preliminary drying, a photo-mask is contacted thereto and light exposure is performed using a super-high pressure mercury lamp to print a pattern. Subsequently, development and washing are carried out, and post-baking is optionally performed. A color filter pattern can thus formed.

Examples of non-photosensitive resin varnish include varnishes of cellulose acetate type resin, nitrocellulose type resin, styrene type polymer, polyvinyl butyral type resin, aminoalkyd resin, polyester type resin, amino resin-modified polyester type resin, polyurethane type resin, acryl polyolurethane type resin, soluble polyamide type resin, soluble polyimide type resin, soluble polyamideimide type resin, soluble polyesterimide type resin, casein, hydroxyethyl cellulose, styrene-maleic acid ester type resin water-soluble salt, (meth-a)acrylic acid ester type (co)polymer, water-soluble aminoalkyd type resin, water-soluble polyester type resin and water-soluble polyamide type resin. These are used alone or in combination.

Using the foregoing non-photosensitive coloring composition, a pattern of a color filter can be formed on the transparent substrate by a method in which using the non-photosensitive colored composition such as a printing ink used for color filters, a colored pattern is printed directly on the transparent substrate by various printing methods, a method of forming a colored pattern on the substrate by electrocoating, using a water-based electrocoating composition, an electronic printing method or an electrostatic printing method. Alternatively, a colored pattern is formed on a transfer substrate by the above-mentioned methods and then transferred to the substrate used for a color filter. Subsequently, baking, polishing for surface-smoothing or top coating for surface protection is optionally conducted according to conventional methods. Black matrix may be formed according to conventional methods to obtain a RGB color filter.

EXAMPLES

The present invention is further described based on examples but embodiments of the invention are by no means limited to these.

First, specific synthesis examples of a few metal complex dyes of the invention are shown below but other dyes of the invention can also synthesized similarly and synthesis methods are not limited to these.

Example 1

Synthesis of Exemplified Compound MD-3

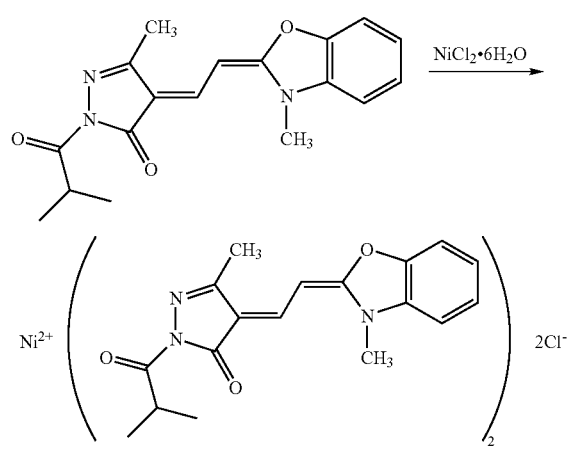

Figure 4:
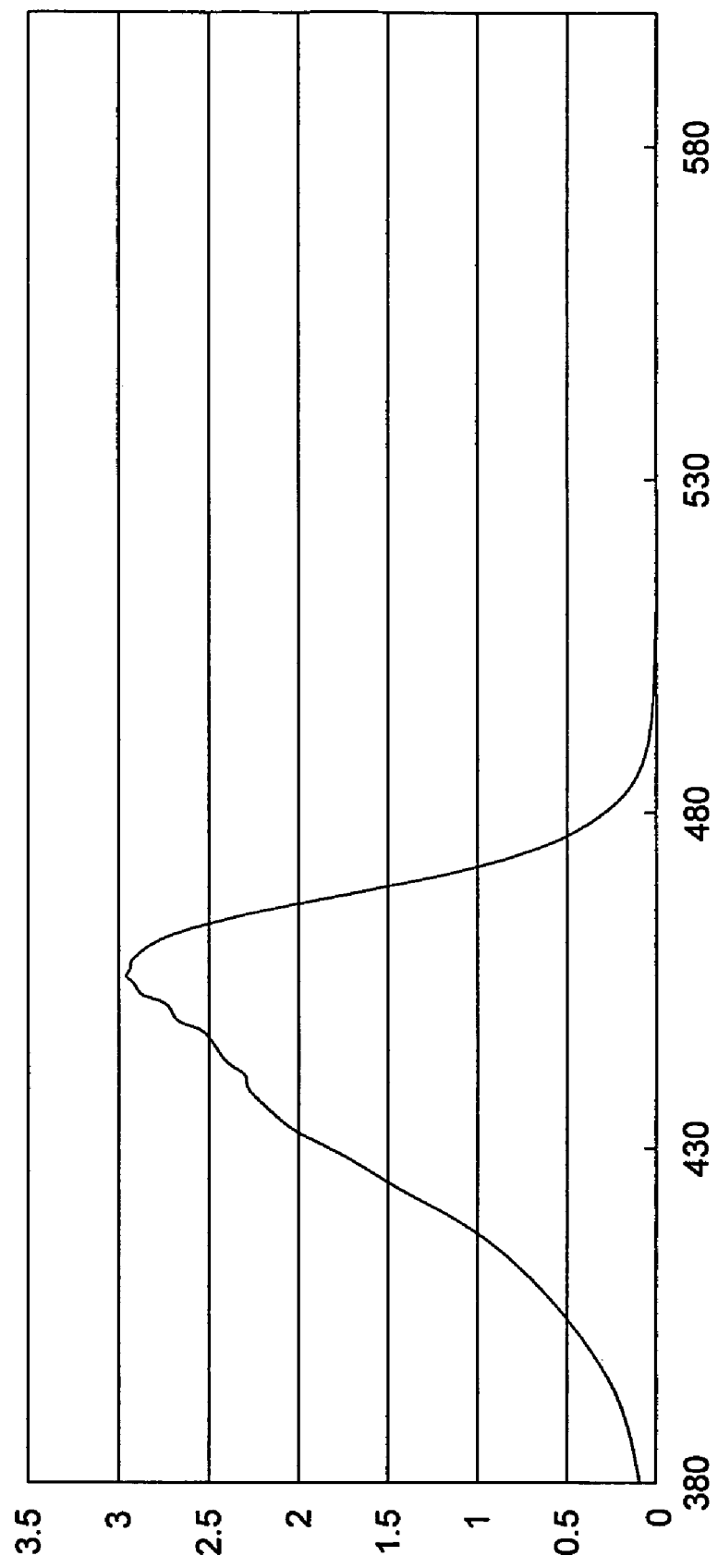
FIGS. 4, 5, 6 and 7 show absorption curves of compounds MD-3, MD-13, MD-64 and MD-33, respectively.

In 25 ml of methanol was dissolved 1.32 g of exemplified compound 13 and 0.48 g of nickel chloride hexahydrate. After distilling oot solvent, acetonitrile was added thereto and crystals were filtered off, washed and dried to obtain 1.10 g of exemplified compound MD-3 (yellow crystal). This compound exhibited an absorption maximum at 458 nm ($\epsilon$=95000) in methanol. The absorption curve in methanol is shown in FIG. 4.

Example 2

Synthesis of Exemplified Compound MD-13

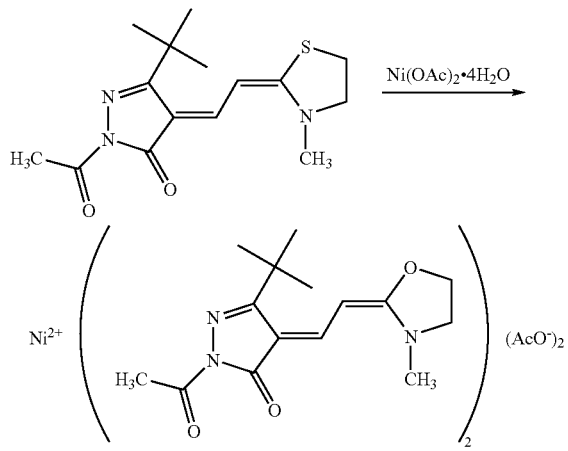

Figure 5:
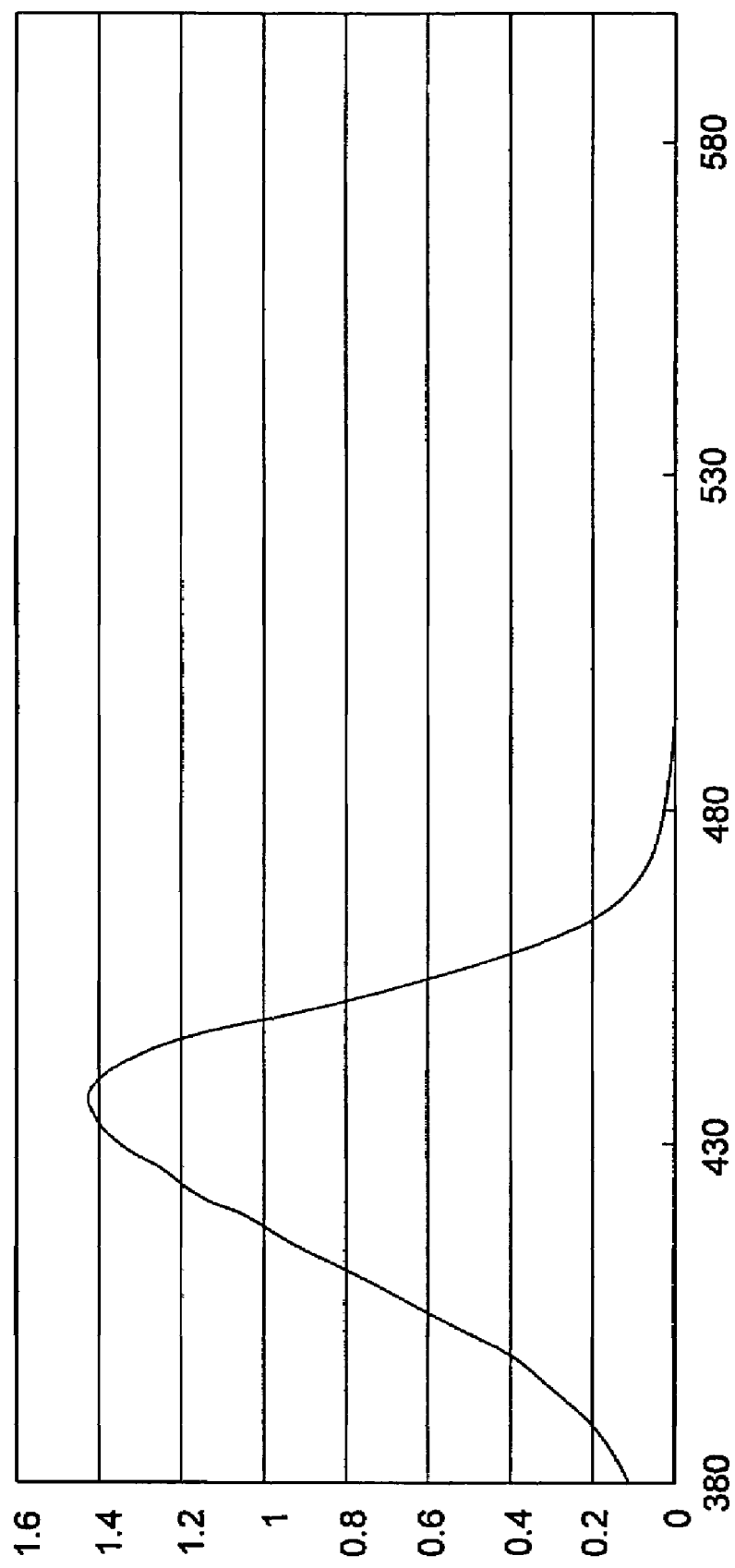

In 25 ml of methanol was dissolved 1.23 g of exemplified compound 52 and 0.50 g of nickel acetate. After distilling out solvent, acetonitrile was added thereto and crystals were filtered off, washed and dried to obtain 1.08 g of exemplified compound MD-13 (yellow crystal). This compound exhibited an absorption maximum at 440 nm ($\epsilon$=45000) in methanol. The absorption curve in methanol is shown in FIG. 5.

Example 3

Synthesis of Exemplified Compound MD-64

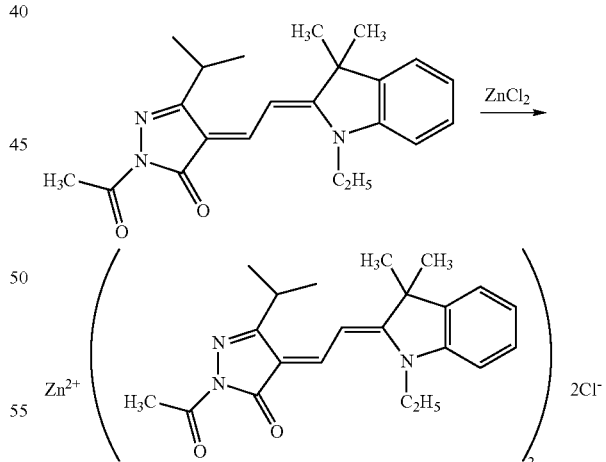

Figure 6:
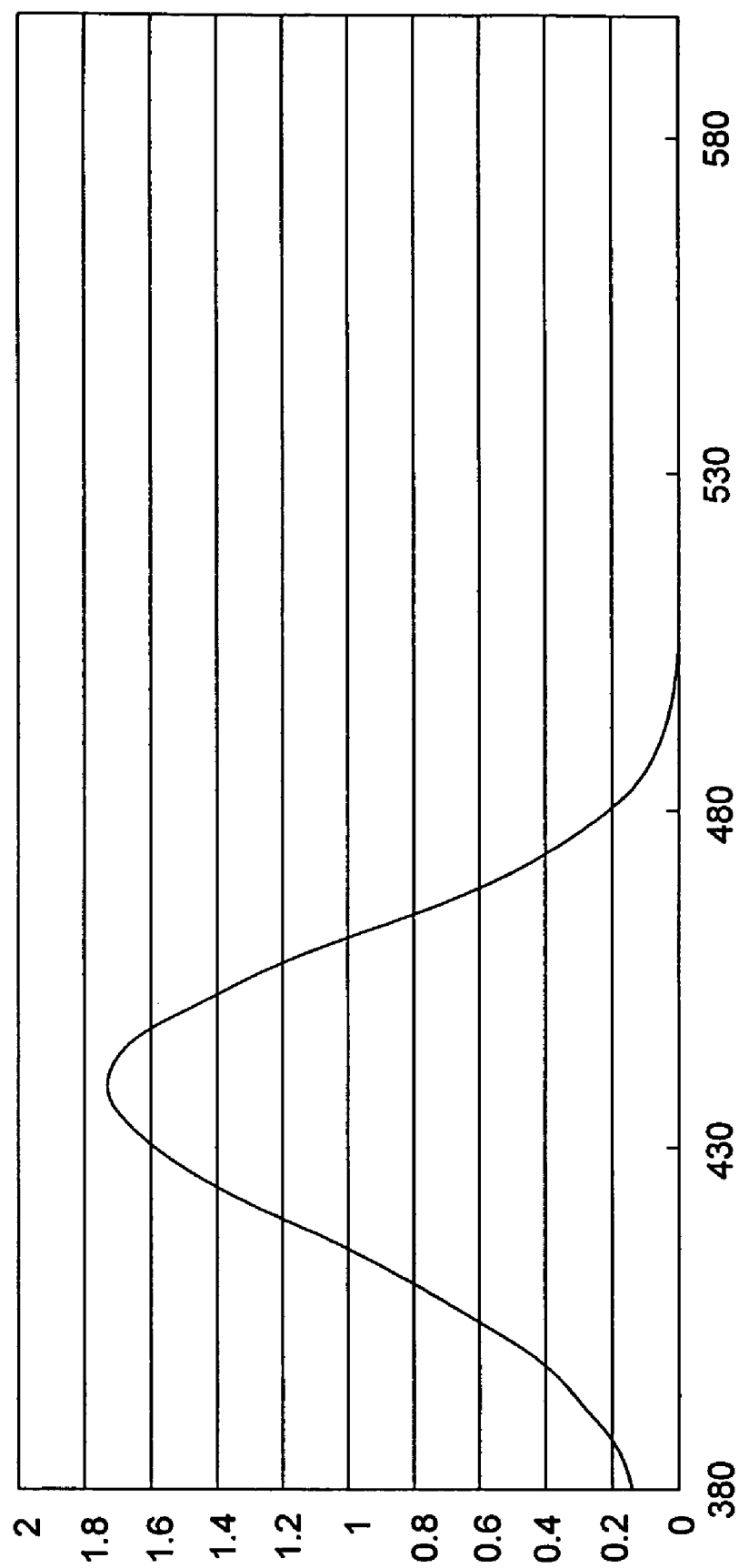

In 25 ml of methanol was dissolved 1.46 g of exemplified compound 80 and 0.27 g of zinc chloride. After completing the addition, precipitation immediately started and the reaction mixture was cooled. Crystals were filtered off, washed and dried to obtain 1.28 g of exemplified compound MD-64 (yellow crystal). This compound exhibited an absorption maximum at 454 nm ($\epsilon$=78000). The absorption curve in methanol is shown in FIG. 6.

Example 4

Synthesis of Exemplified Compound MD-33

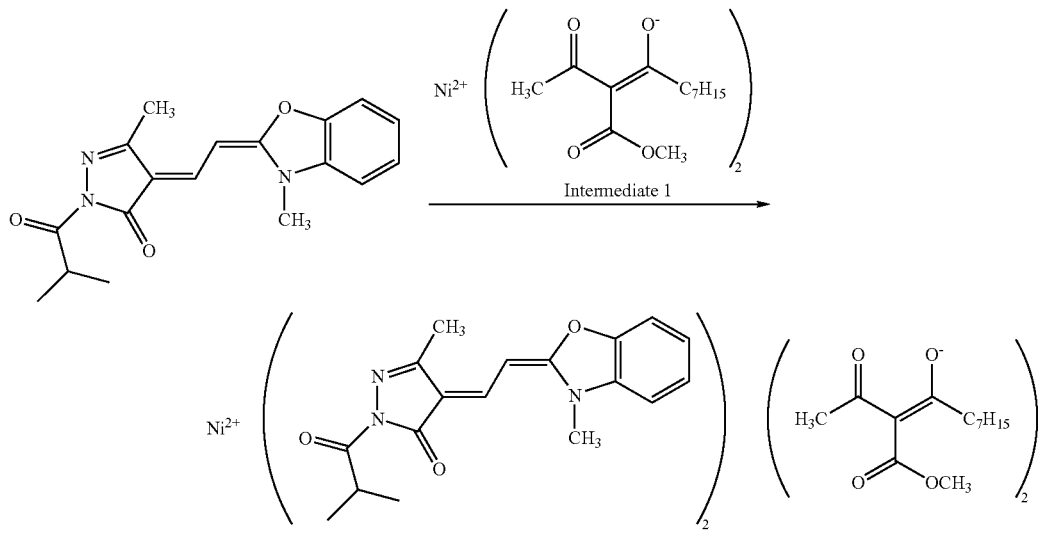

Figure 7:
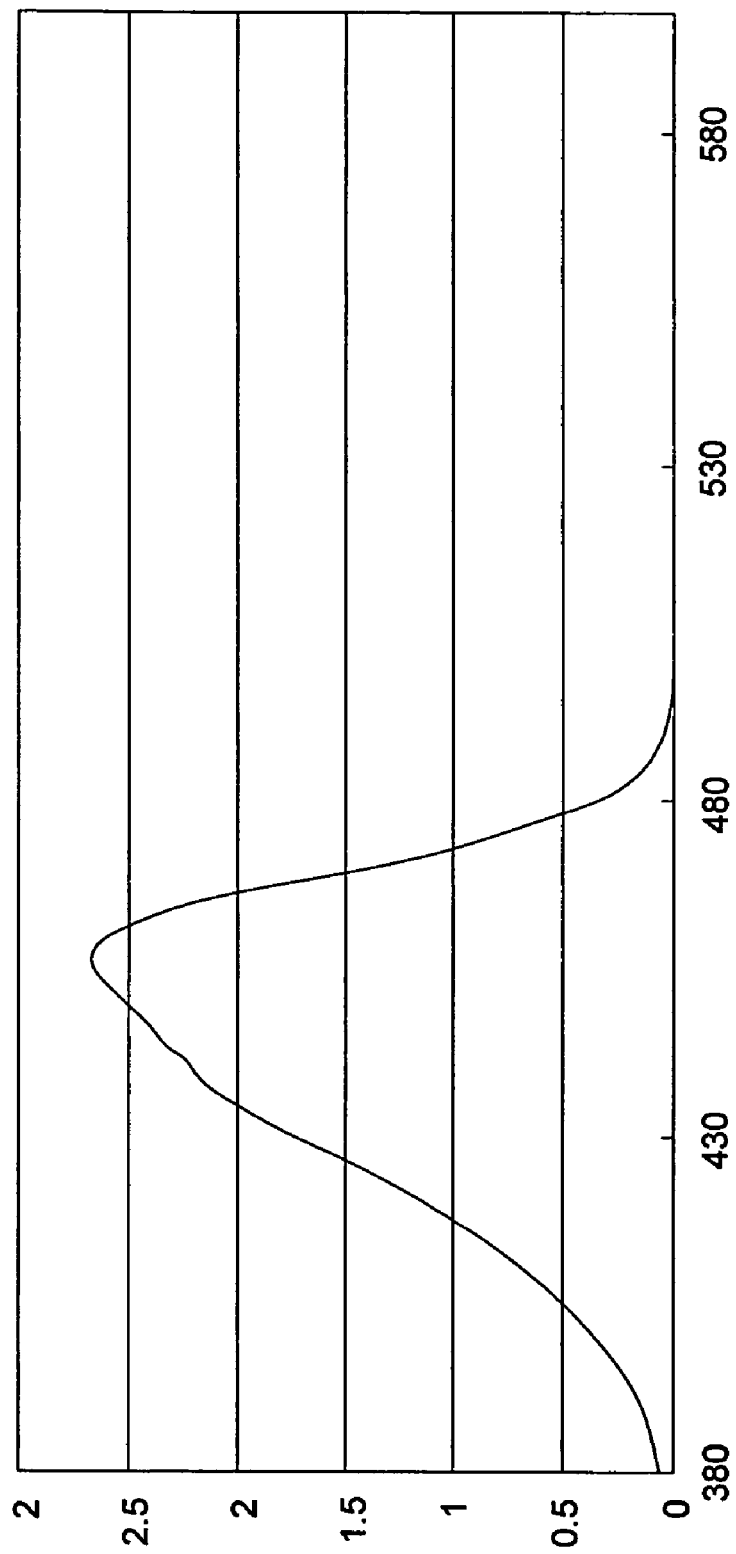

In 25 ml of methanol was dissolved 1.32 g of exemplified compound 13 and 1.20 g of intermediate 1. After distilling out solvent, acetonitrile was added thereto and crystals were filtered off, washed and dried to obtain 1.81 g of exemplified compound MD-33 (yellow crystal). This compound exhibited an absorption maximum at 458 nm ($\epsilon$=97000) in methanol. The absorption curve in methanol is shown in FIG. 7.

Dyes shown in Examples 1 to 4 each exhibited a high extinction coefficient ($\epsilon$) and superior color.

Example 5

Preparation of Color Toner: Pulverization Method

Polyester resin of 100 parts, 8 parts of a metal complex dye shown in Table 2 and 3 parts of polypropylene were mixed, kneaded, pulverized and classified to obtain a powder of an average particle size of 8.5 μm. Further, 100 parts of this powder and 1.0 part of particulate silica (particle size of 12 μm, hydrophobic degree of 60) were mixed by Henschel mixer to obtain a color toner.

Preparation of Color Toner: Polymerization Method

In 200 ml of pure water was dissolved 5 g of sodium dodecyl sulfate. To this aqueous solution, 20 g of a metal complex dye shown in Table 2 was added. Using a stirrer and a ultrasonic homogenizer, the obtained aqueous yellow colorant dispersion and a low molecular weight polypropylene (number-average molecular weight=3200) were emulsified in water with a surfactant, while heating so that the solid content was 30%. Thus, an emulsified dispersion was prepared.

To the foregoing dye dispersion, 60 g of an emulsion of low molecular weight polypropylene was added and mixed, and further thereto, 220 g of styrene monomer, 40 g of n-butylacrylate monomer, 12 g of methacrylic acid monomer, 5.4 g of t-dodecylmercaptane as a chain-transfer agent and 2000 ml of degassed pure water were added and maintained at 70° C. for 3 hr. with stirring in a stream of nitrogen to perform emulsion polymerization.

To 1000 ml of the thus obtained particulate resin dispersion containing a yellow dye, sodium hydroxide was added to adjust the pH to 7.0. Thereafter, 270 ml of aqueous 2.7 mol % potassium chloride solution was added, and 160 ml of isopropyl alcohol and aqueous solution of 9.0 g of polyoxyethylene octylphenyl ether (having a mean ethyleneoxide polymerization degree of 10) dissolved in 9.0 g of pure water were added thereto and maintained at 75° C. for 6 hr. to perform reaction. The obtained reaction mixture was filtered, washed, and then dried and pulverized to obtain colored particles. The obtained colored particles and 1.0 part of particulate silica (particle size of 12 μm, hydrophobic degree of 60) were mixed by a Henschel mixer to obtain a color toner.

To 10 parts of the obtained toner, 900 parts of carrier iron powder (trade name EFV250/400, produced by Nippon Teppun Co., Ltd) was added and mixed to obtain a developer. Similarly, developer samples were prepared, provided that 3 parts by weight of a metal complex dye shown in Table 2 was used. Using these developers, copying was conducted by dry plain paper electrophotographic copier (trade name: NP-5000, produced By CANON INC.)

Evaluation tests were conducted in such a manner that using developers of the foregoing toners, reflection-type images and transmission-type images were prepared on paper and OHP, respectively, by the image formation method described above and evaluated as below. Evaluation was made at a toner coverage of 0.7±0.05 mg/cm$^2$. Obtained images were evaluated with respect to color and lightfastness. Color was visually evaluated based on the following criteria:

A: excellent color

B: favorable color

C: inferior color.

Lightfastness was evaluated in the manner that immediately after recording, the image density (Ci) was measured and after exposed to Xenon light (85,000 lux) for 5 days in a weather-meter, image density (Cf) was again measured and the residual dye ratio was determined from the difference in image density between before and after exposure to xenon light, according to the equation:

$$\{(Ci-Cf)/Ci\} \times 100(\%)$$

and evaluated based on the following criteria:

A: residual ratio of 95% or more,

B: residual ratio of 90% to 95%,

C: residual ratio of 80% to 90%,

D: residual ratio of less than 80%.

The image density was measured using reflection densitometer (X-Rite 310TR). Evaluation results are shown in Table 2.

Transparency of an OHP image was evaluated in the following manner. The visual spectral transmittance of the image was measured using self-recording spectrophotometer Type 330, produced by HITACHI with reference to OHP sheet having no toner to determine spectral transmittance at 650 nm as a measure of transparency of OHP images. Evaluation was made based on the following criteria:

A: transmittance of 80% or more

B: transmittance of 70% to 80%

C: transmittance of less than 70%.

TABLE 2

| Color Toner | Metal Complex Dye | Color | Light-fastness | Transparency | Preparation | Remark |
|---|---|---|---|---|---|---|
| 1 | MD-3 | B | B | B | Pul. | Inv. |
| 2 | MD-6 | B | B | C | Pul. | Inv. |
| 3 | MD-26 | B | C | B | Pul. | Inv. |
| 4 | MD-1 | B | B | B | Pol. | Inv. |
| 5 | MD-3 | B | A | B | Pol. | Inv. |
| 6 | MD-4 | B | A | B | Pol. | Inv. |
| 7 | MD-6 | B | B | B | Pol. | Inv. |
| 8 | MD-15 | B | A | B | Pol. | Inv. |
| 9 | MD-22 | B | A | B | Pol. | Inv. |
| 10 | MD-33 | B | A | B | Pol. | Inv. |
| 11 | MD-37 | B | B | B | Pol. | Inv. |
| 12 | MD-39 | B | A | B | Pol. | Inv. |
| 13 | MD-42 | B | B | B | Pol. | Inv. |
| 14 | MD-48 | B | A | B | Pol. | Inv. |
| 15 | MD-56 | C | A | B | Pol. | Inv. |
| 16 | MD-60 | B | A | B | Pol. | Inv. |
| 17 | MD-74 | B | A | B | Pol. | Inv. |
| 18 | MD-79 | B | B | C | Pol. | Inv. |
| 19 | Comp. Dye 1 | C | C | C | Pul. | Comp. |
| 20 | Comp. Dye 1 | B | C | C | Pol. | Comp. |
| 21 | C.I. Pigment Yellow 10 | D | A | D | Pul. | Comp. |
| 22 | C.I. Pigment Yellow 10 | D | A | D | Pol. | Comp. |

*1 Pul.: Pulverization method
*2 Pol.: Polymerization method
Comp. Dye 1

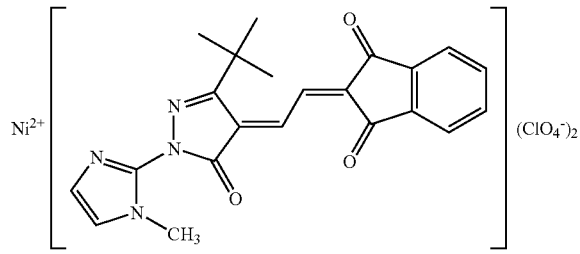

As apparent from Table 2, the use of color toners of the invention resulted in to faithful color reproduction and superior OHP quality and the toners of the invention were suitable as a full color toner. Further lightfastness was superior, providing images which can be preserved over a long period.

Example 6

Color Filter

A color filter was prepared in the manner described below. A positive-type resist composition containing a quinoneazide compound, a cross-linking agent, a dye and a solvent was coated by a spin coater on a silicon wafer, a thermo-setting resin. After evaporating the solvent with heating, exposure was conducted through a mask to decompose the quinone azide compound. Heating was optionally applied and then development was conducted to obtain mosaic pattern. Exposure was conducted using i-line exposure stepper HITACHI LD-5010-I (Na=0.40), produced by HITACHI. Developer SOPD or SOPD-B (produced by Sumitomo Kagaku Kogyo Co., Ltd.) was used.

Positive-Type Resist Composition

Positive-type resist composition was prepared using 3.4 parts by weight of cresol novolac resin (polystyrene-converted weight-average molecular weight: 4300) obtained from a mixture of m-cresol/p-cresol/formaldehyde (reaction molar ratio=5/5/7.5), and a phenol compound as shown below.

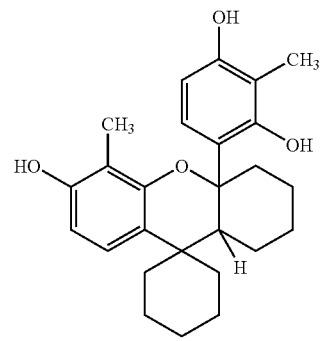

The positive-type resist composition was prepared using 1.8 parts by weight of o-naphthoquinone-di-azido-5-sulfonic acid ester (in which two hydroxy group on average was esterified) 0.8 part by weight of hexamethoxymethylol-modified melamine, 20 parts by weight of ethyl lactate and 1 part by weight of a metal complex dye as shown in Table 3.

The thus obtained positive-type resist composition was coated on a silicon wafer by a spin coater and then the solvent was evaporated. After exposed, the silicon wafer was subjected to alkaline development to obtain positive-type colored pattern exhibiting a resolving power of 1 μm. This was subjected to overall exposure and heated at 150° C. for 15 min. to obtain a yellow complimentary color filter.

Similarly to the foregoing, a positive-type resist composition was prepared, provided that the metal complex dye was replaced by 1 part by weight of Comp. Dye 2. The prepared positive-type resist composition was coated on a silicon wafer by a spin coater and then the solvent was evaporated. After exposed, the silicon wafer was subjected to alkaline development to obtain positive-type colored pattern exhibiting a resolving power of 1 μm. This was subjected to overall exposure and heated at 150° C. for 10 min. to obtain a yellow complimentary color filter for comparison.

Evaluation

The thus obtained yellow color filters were each subjected to transmission spectrometry and evaluated with respect to absorption characteristic, that is, sharpness of the longer wavelength side of the absorption spectrum which was important in color reproduction, based on the following criteria:

A: superior sharpness,
B: slightly inferior sharpness,
C: inferior sharpness.

Further, using a weather meter (Atlas. C. I65), exposure to xenon light (85000 lx) was performed over a period of 7 days. Then, the difference in image density between before and after exposure to xenon light was measured to determine the residual dye ratio as a measure of lightfastness. Results are shown in Table 3.

TABLE 3

| Color Filter | Metal Complex Dye | Absorption Characteristic | Light-fastness | Remark |
|---|---|---|---|---|
| 1 | MD-3 | A | 88% | Inv. |
| 2 | MD-4 | A | 90% | Inv. |
| 3 | MD-6 | A | 82% | Inv. |
| 4 | MD-13 | A | 93% | Inv. |
| 5 | MD-28 | A | 80% | Inv. |
| 6 | MD-33 | A | 95% | Inv. |
| 7 | MD-36 | A | 85% | Inv. |
| 8 | MD-46 | A | 94% | Inv. |
| 9 | MD-49 | A | 94% | Inv. |
| 10 | MD-66 | A | 92% | Inv. |
| 11 | MD-75 | A | 86% | Inv. |
| 12 | MD-81 | B | 82% | Inv. |
| 13 | MD-84 | B | 80% | Inv. |
| 14 | Comp. Dye 2 | B | 63% | Comp. |

Comp. Dye 2

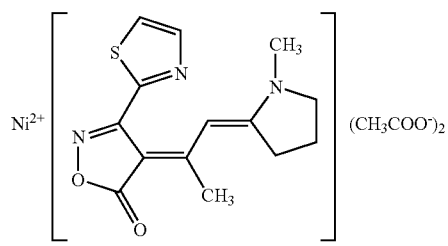

As apparent from Table 3, color filters using the dyes of the invention exhibited the absorption of the longer wavelength side being sharp and resulted in superior color reproduction, as compared to the comparative color filter. The dyes of the invention were superior in lightfastness to the comparative dye.

What is claimed is:

1. A metal complex dye containing a ligand represented by: one of the following formulas (1a) to (1d):

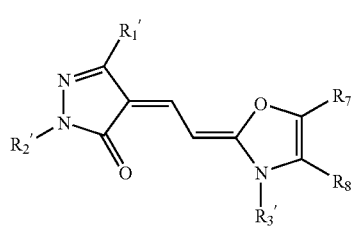

formula (1a)

-continued

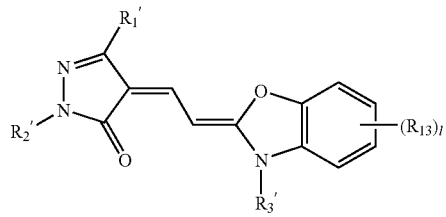

formula (1b)

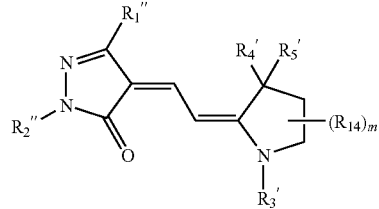

formula (1c)

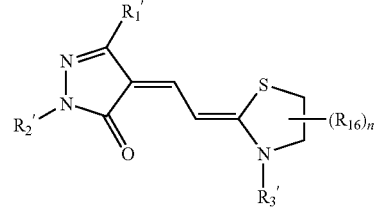

formula (1d)

wherein $R_1'$ is an alkyl group; $R_2'$ is, an acyl group or a carbamoyl group; $R_3'$ is an alkyl group, an alkenyl group or aryl group; $R_7$ and $R_8$ are each a hydrogen atom, a halogen atom or a substituent, provided that $R_7$ and $R_8$ may combine with each other to form a ring; $R_{13}$ is a halogen atom or a substituent; 1 is an integer of 0 to 4; $R_1''$ is trifluoromethyl, an alkoxycarbonyl group, or cyano group; $R_2''$ is an alkyl group, an acyl group or a carbamoyl group, provided that the total number of carbon atoms of $R_1''$ and $R_2''$ is 3 or more; $R_4'$ and $R_5'$ are each a hydrogen atom, a halogen atom or a substituent; $R_{14}$ and $R_{15}$ are each a halogen atom or a substituent; and m and n are each an integer of 0 to 4.

2. The metal complex dye of claim 1, wherein the metal complex dye contains $Cu^{2+}$, $Ni^{2+}$ or $Zn^{2+}$ as a central metal ion.

3. The metal complex dye of claim 1, wherein the metal complex dye further contains a ligand represented by the following formula (2):

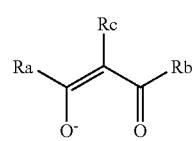

formula (2)

wherein Rc is an alkyl group, an aryl group, an alkoxy group, an acyl group, an alkoxycarbonyl group, an aryloxycarbonyl group, a carbamoyl group, a halogen atom or a hydrogen atom; Ra and Rb are each an alkyl group or an aryl group, provided that Ra and Rc, or Rb and Rc may combine with each other to form a ring and when Rc is a hydrogen atom, Ra and Rb are not methyl groups at the same time.

4. A color toner comprising a metal complex dye as claimed in claim 1.

5. A color filter comprising a metal complex dye as claimed in claim 1.

* * * * *

UNITED STATES PATENT AND TRADEMARK OFFICE
CERTIFICATE OF CORRECTION

| | |
|---|---|
| PATENT NO. | : 7,595,139 B2 |
| APPLICATION NO. | : 11/206490 |
| DATED | : September 29, 2009 |
| INVENTOR(S) | : Koji Daifuku |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Third Day of May, 2011

David J. Kappos
*Director of the United States Patent and Trademark Office*